US010350636B2

(12) United States Patent
Kandori

(10) Patent No.: US 10,350,636 B2
(45) Date of Patent: Jul. 16, 2019

(54) CAPACITIVE TRANSDUCER AND SAMPLE INFORMATION ACQUISITION APPARATUS

(71) Applicant: CANON KABUSHIKI KAISHA, Tokyo (JP)

(72) Inventor: Atsushi Kandori, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 75 days.

(21) Appl. No.: 14/945,337

(22) Filed: Nov. 18, 2015

(65) Prior Publication Data

US 2016/0144402 A1    May 26, 2016

(30) Foreign Application Priority Data

Nov. 20, 2014 (JP) ................. 2014-236048

(51) Int. Cl.
*G01N 29/00* (2006.01)
*B06B 1/02* (2006.01)
*G01N 29/22* (2006.01)
*G01N 29/24* (2006.01)
*G01N 29/44* (2006.01)

(52) U.S. Cl.
CPC ......... *B06B 1/0292* (2013.01); *G01N 29/221* (2013.01); *G01N 29/2406* (2013.01); *G01N 29/2418* (2013.01); *G01N 29/44* (2013.01)

(58) Field of Classification Search
CPC .... G01N 29/22; G01N 29/24; G01N 15/0656; G01N 29/221; G01N 29/2406; G01N 29/2418; G01N 29/44; B06B 1/0292
USPC .......................................................... 73/632
See application file for complete search history.

(56) References Cited

U.S. PATENT DOCUMENTS

| 3,749,948 | A | 7/1973 | Morris |
| 6,359,367 | B1* | 3/2002 | Sumanaweera ....... B06B 1/0292 310/306 |
| 6,562,650 | B2* | 5/2003 | Ladabaum ............ B06B 1/0292 310/334 |
| 6,773,401 | B1* | 8/2004 | Dreschel .................. B06B 1/00 600/459 |
| 6,831,394 | B2* | 12/2004 | Baumgartner ........ B06B 1/0292 310/311 |
| 6,933,059 | B1* | 8/2005 | Beamer .................... B32B 7/02 428/344 |

(Continued)

FOREIGN PATENT DOCUMENTS

| CN | 101238754 A | 8/2008 |
| CN | 102281818 A | 12/2011 |

(Continued)

OTHER PUBLICATIONS

Arif Sanh Ergun, et al.; "Capacitive Micromachined Ultrasonic Transducers: Fabrication Technology"; IEEE Transaction on Ultrasonics, Ferroelectrics, and Frequency Control; Dec. 2005; pp. 2242-2258; vol. 52, No. 12.

*Primary Examiner* — Max H Noori
(74) *Attorney, Agent, or Firm* — Canon U.S.A., Inc. IP Division

(57) ABSTRACT

A capacitive transducer includes at least one cell that includes a first electrode and a vibrating membrane including a second electrode provided so as to be apart from the first electrode with a cavity sandwiched between the first electrode and the second electrode. An electrostatic shield is provided on the cell via a silicone rubber layer.

27 Claims, 21 Drawing Sheets

(56) References Cited

U.S. PATENT DOCUMENTS

| | | | | |
|---|---|---|---|---|
| 7,087,023 B2* | 8/2006 | Daft | | B06B 1/0292 600/459 |
| 7,427,825 B2* | 9/2008 | Frey | | B06B 1/0292 310/366 |
| 7,580,172 B2* | 8/2009 | Lewis | | B81B 7/0006 359/245 |
| 7,754,595 B2* | 7/2010 | Enomoto | | G01S 7/52079 257/E21.008 |
| 7,804,970 B2* | 9/2010 | Hippe | | B06B 1/0622 310/334 |
| 7,951,634 B2* | 5/2011 | Floyd | | B81B 7/0012 359/295 |
| 8,477,983 B2* | 7/2013 | Weigold | | H04R 1/406 381/174 |
| 9,310,485 B2* | 4/2016 | Degertekin | | G01S 15/89 |
| 9,497,552 B2* | 11/2016 | Akiyama | | H04R 19/013 |
| 2001/0051298 A1* | 12/2001 | Hanafusa | | H01M 2/0207 429/162 |
| 2005/0203409 A1* | 9/2005 | Frey | | B06B 1/0292 600/459 |
| 2008/0089181 A1* | 4/2008 | Adachi | | A61B 8/12 367/189 |
| 2008/0290756 A1* | 11/2008 | Huang | | B06B 1/0292 310/300 |
| 2009/0005685 A1* | 1/2009 | Nagae | | A61B 5/0059 600/459 |
| 2009/0140357 A1* | 6/2009 | Kupnik | | B06B 1/0292 257/416 |
| 2011/0182149 A1* | 7/2011 | Kandori | | B06B 1/0292 367/189 |
| 2012/0316445 A1* | 12/2012 | Machida | | B06B 1/0292 600/459 |
| 2013/0051587 A1* | 2/2013 | Stephanou | | G01H 11/08 381/190 |
| 2013/0127065 A1* | 5/2013 | Degertekin | | B06B 1/0292 257/774 |
| 2014/0116139 A1* | 5/2014 | Endo | | B06B 1/0622 73/584 |
| 2014/0116140 A1* | 5/2014 | Endo | | B06B 1/0207 73/584 |
| 2014/0318255 A1* | 10/2014 | Torashima | | B06B 1/0292 73/627 |
| 2015/0016222 A1* | 1/2015 | Kandori | | H05K 1/025 367/87 |
| 2015/0027228 A1* | 1/2015 | Endo | | G01N 29/262 73/641 |
| 2015/0029818 A1* | 1/2015 | Endo | | A61B 8/13 367/7 |
| 2016/0144402 A1* | 5/2016 | Kandori | | B06B 1/0292 73/632 |
| 2016/0153939 A1* | 6/2016 | Kato | | B06B 1/0292 73/606 |
| 2017/0067856 A1* | 3/2017 | Kandori | | G01N 29/0654 |
| 2017/0156696 A1* | 6/2017 | Takezaki | | A61B 8/4483 |

FOREIGN PATENT DOCUMENTS

| | | |
|---|---|---|
| CN | 103521421 A | 1/2014 |
| CN | 104145179 A | 11/2014 |
| EP | 2682196 A1 | 1/2014 |
| WO | 2009/139400 A1 | 11/2009 |

* cited by examiner

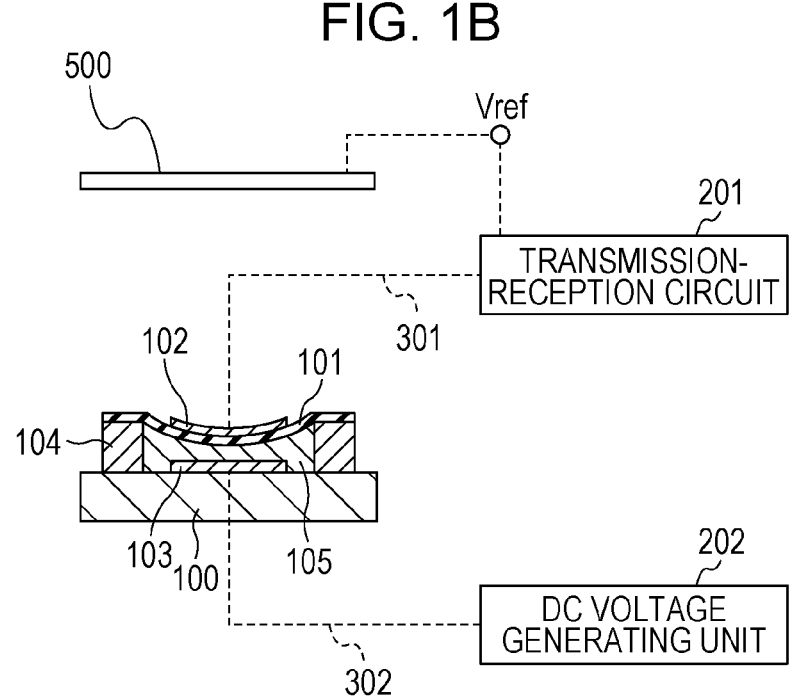

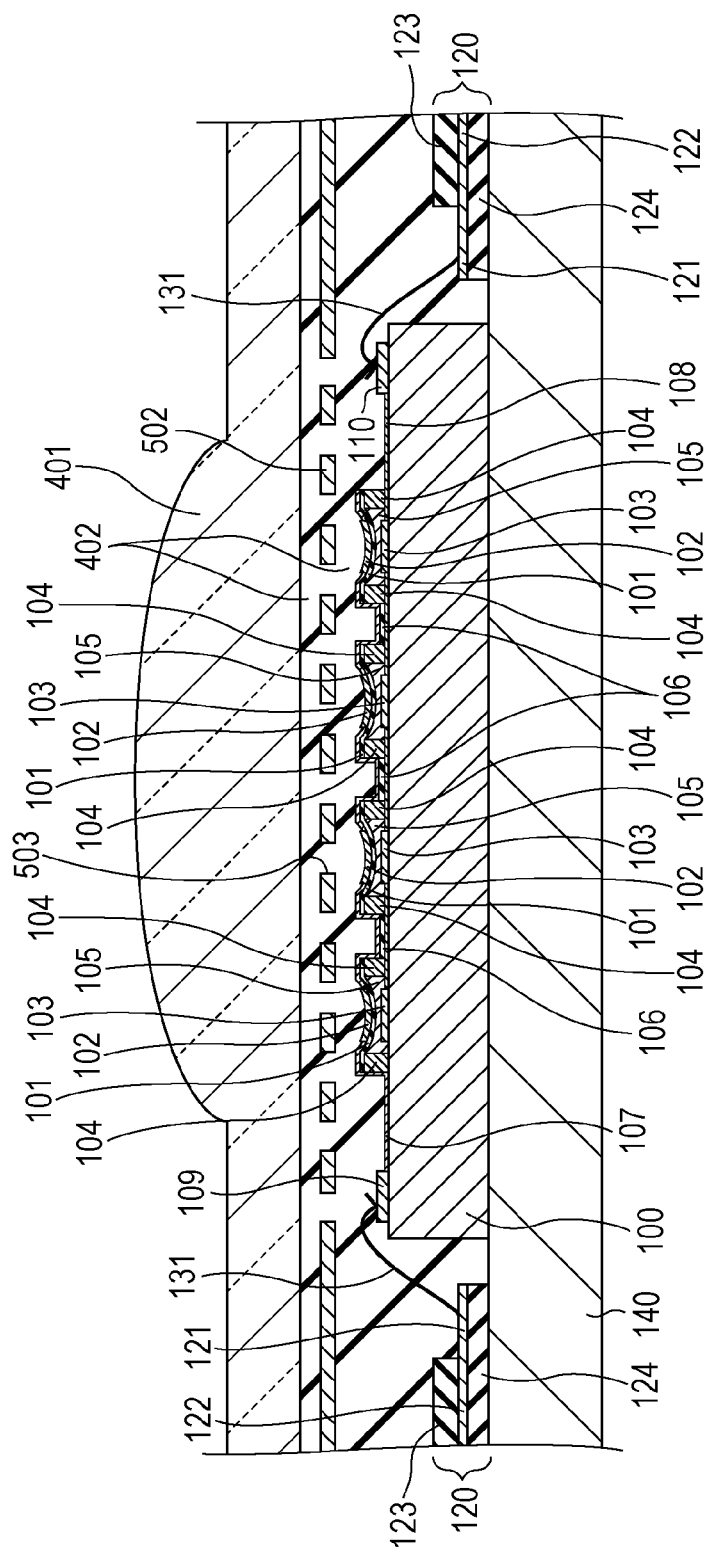

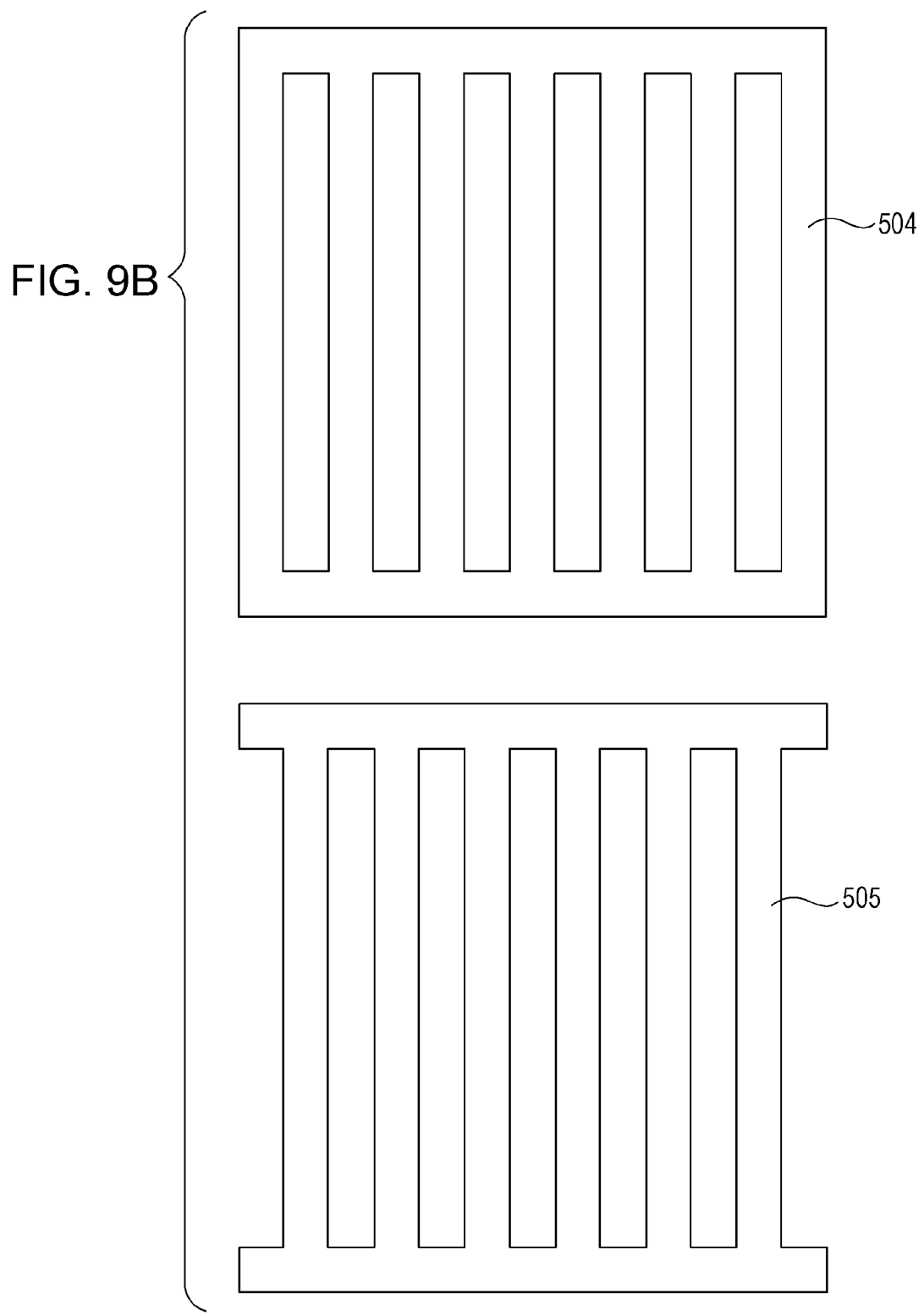

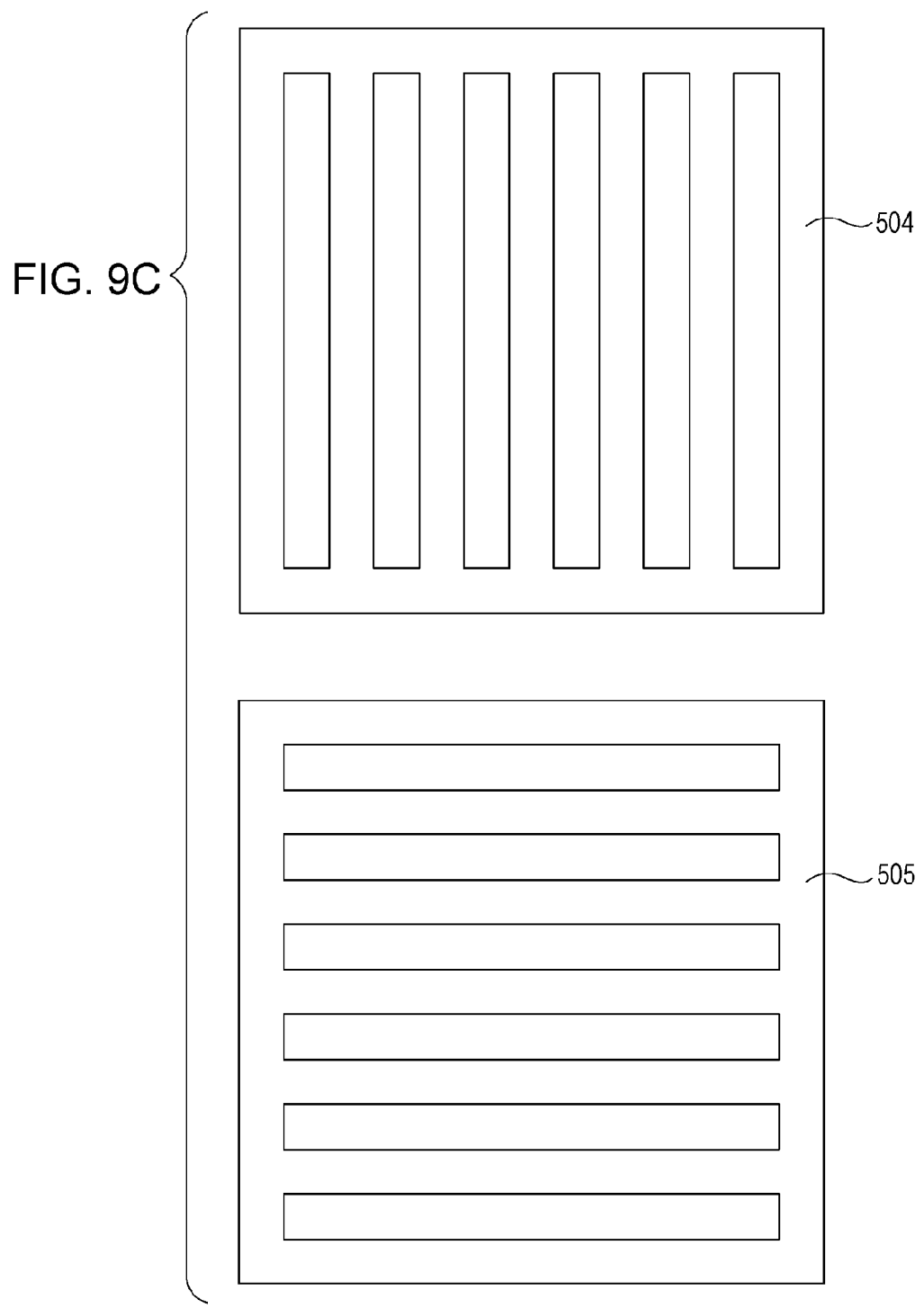

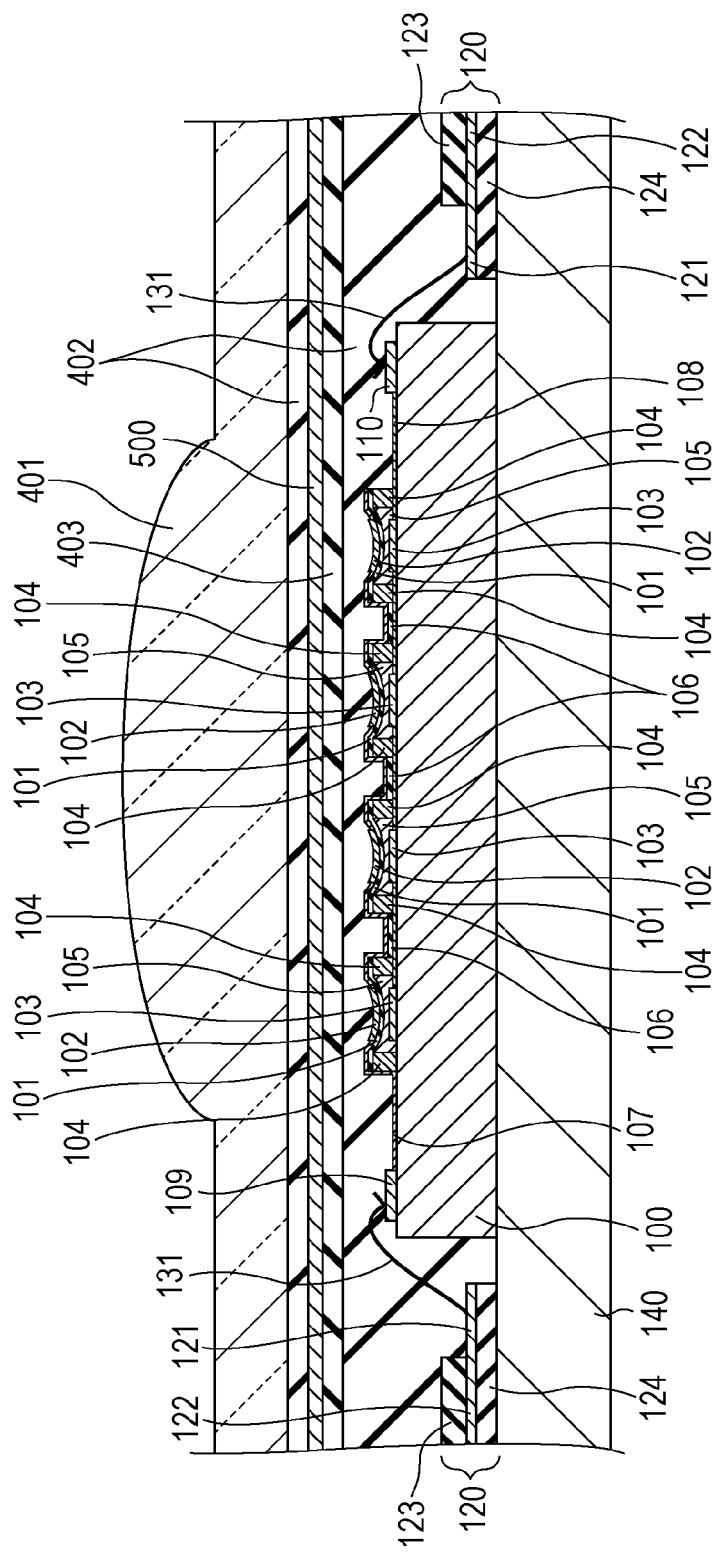

CAPACITIVE TRANSDUCER AND SAMPLE INFORMATION ACQUISITION APPARATUS

BACKGROUND OF THE INVENTION

Field of the Invention

The present invention relates to a capacitive electromechanical conversion device or transducer that performs transmission and reception of acoustic waves, such as ultrasonic waves, and a sample information acquisition apparatus using the capacitive electromechanical conversion device or transducer. The transmission and reception in this specification means at least one of transmission and reception. Although the acoustic waves are used as a term including sound waves, ultrasonic waves, and photoacoustic waves, the acoustic waves may be typified by the ultrasonic waves.

Description of the Related Art

Capacitive Micromachined Ultrasonic Transducers (CMUTs) have been proposed as transducers that performs transmission and reception of the ultrasonic waves (refer to A. S. Ergun, Y. Huang, X. Zhuang, O. Oralkan, G. G. Yarahoglu, and B. T. Khuri-Yakub, "Capacitive micromachined ultrasonic transducers: fabrication technology," Ultrasonics, Ferroelectrics and Frequency Control, IEEE Transactions on, vol. 52, no. 12, pp. 2242-2258, December 2005). The CMUTs are manufactured using a Micro Electro Mechanical Systems (MEMS) process that applies a semiconductor process. FIG. 13 is a schematic cross-sectional view of an exemplary CMUT (transmission-reception element). Referring to FIG. 13, a set of a vibrating membrane 101, and a first electrode 102 and a second electrode 103, which are opposed to each other with a cavity 105 sandwiched therebetween, is referred to as a cell. The vibrating membrane 101 is supported by supporters 104 formed on a chip 100. A direct-current voltage generating unit 202 is connected to the second electrode 103. Certain direct-current voltage Va is applied from the direct-current voltage generating unit 202 to the second electrode 103 via a second conductive line 302. The first electrode 102 is connected to a transmission-reception circuit 201 via a first conductive line 301 and has fixed potential near ground (GND) potential. This causes a potential difference of Vbias=Va−0V between the first electrode 102 and the second electrode 103. Adjusting the value of the direct-current voltage Va causes the value of Vbias to coincide with a desired potential difference (around several ten volts to several hundred volts) determined on the basis of mechanical characteristics of the CMUT cells.

Application of alternating-current drive voltage to the first electrode 102 from the transmission-reception circuit 201 causes alternating-current electrostatic attractive force between the first electrode 102 and the second electrode 103 and causes the vibrating membrane 101 to vibrate at a certain frequency to transmit the ultrasonic waves. The vibration of the vibrating membrane 101 in response to the ultrasonic waves causes weak current in the first electrode 102 through electrostatic induction. Measurement of the value of the current with the transmission-reception circuit 201 allows a reception signal to be extracted. The potential difference between the CMUT electrodes causes the electrostatic attractive force between the electrodes to decrease the distance between the electrodes. Increase in electric field strength between the electrodes increases transmission sound pressure (transmission efficiency) when the same drive voltage is applied and increases an output signal (reception sensitivity) when the same ultrasonic waves are received.

SUMMARY OF THE INVENTION

It may be necessary to improve transmission and reception characteristics when a capacitive ultrasonic transducer (CMUT) is used in contact with a sample (charged sample), such as a living body. The present invention provides a capacitive transducer having excellent transmission and reception characteristics and a sample information acquisition apparatus using the capacitive transducer.

A capacitive transducer includes at least one cell that includes a first electrode and a vibrating membrane including a second electrode provided so as to be apart from the first electrode with a cavity sandwiched between the first electrode and the second electrode; a silicone rubber layer; and an electrostatic shield provided on the cell via the silicone rubber layer.

Further features of the present invention will become apparent from the following description of exemplary embodiments with reference to the attached drawings.

BRIEF DESCRIPTION OF THE DRAWINGS

FIGS. 1A and 1B are cross-sectional views for describing a capacitive transducer according to a first embodiment.

FIG. 8A is a cross-sectional view for describing a capacitive transducer according to a fifth embodiment.

FIG. 9B is a top view for describing an exemplary electrostatic shield of the sixth embodiment.

FIG. 9C is a top view for describing another exemplary electrostatic shield of the sixth embodiment.

FIGS. 10A and 10B are cross-sectional views for describing a capacitive transducer according to a seventh embodiment.

DESCRIPTION OF THE EMBODIMENTS

In embodiments of the present invention, in order to resolve the above problem, an electrostatic shield, such as a metal layer, having predetermined fixed potential is arranged between the surface of a transducer facing a sample and capacitive cells arranged on a chip or substrate. The metal layer is a typical example of the electrostatic shield. The electrostatic shield is not necessarily made of metal because it is sufficient for the electrostatic shield to have conductivity. However, since the electrostatic shield is desirably thin so as not to have undesired effects on the transmission characteristics of the ultrasonic waves when the electrostatic shield is actually used, it is preferred that the electrostatic shield be made of metal. While the embodiments of the invention will be described below, it will be recognized and understood that the present invention is not limited to the embodiments and that various modifications and changes may be made in the invention within the spirit and scope of the invention.

The embodiments of the present invention will herein be described with reference to the attached drawings.

<First Embodiment>

Figure 1A:
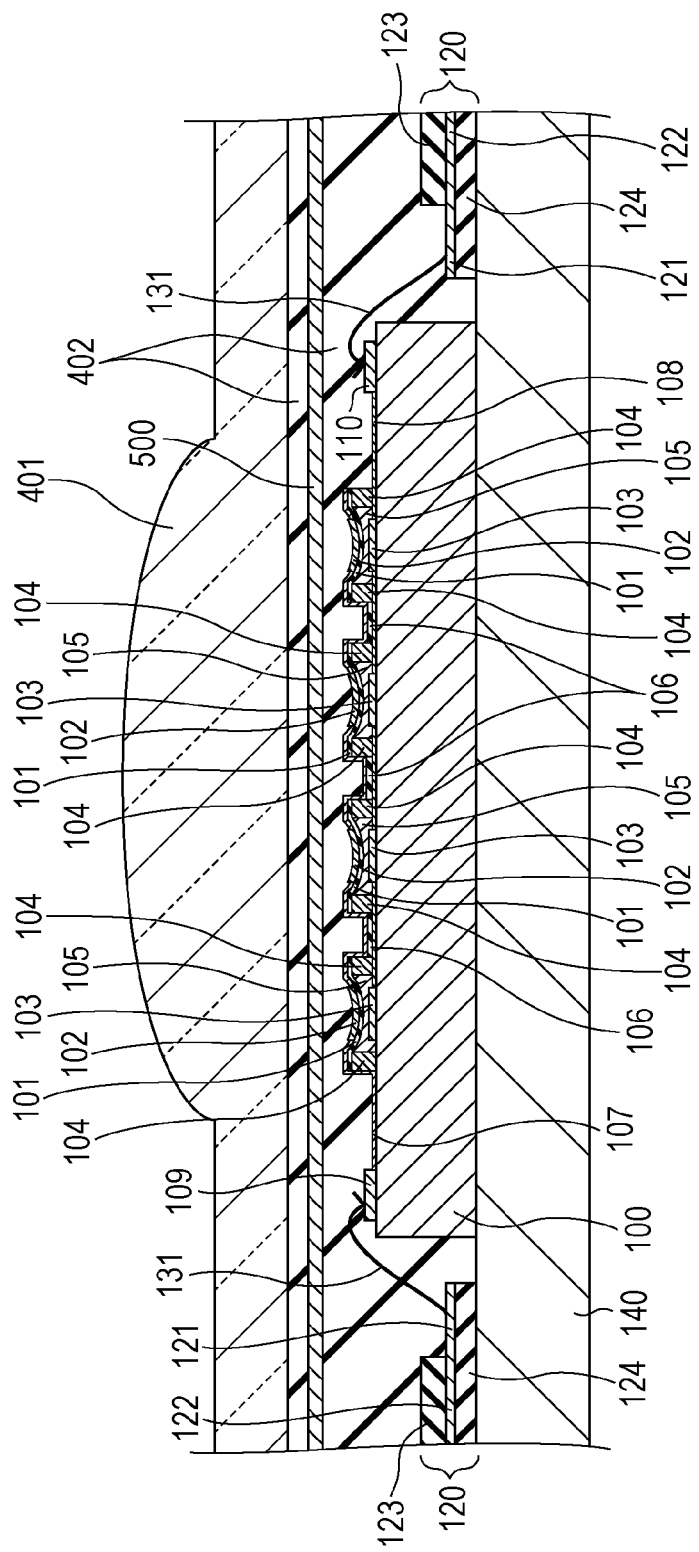

FIGS. 1A and 1B are schematic cross-sectional views of a capacitive transducer according to a first embodiment of the present invention. Referring to FIG. 1A, reference numeral 100 denotes a chip or substrate, reference numeral 101 denotes a vibrating membrane, reference numeral 102 denotes a first electrode, reference numeral 103 denotes a second electrode, reference numeral 104 denotes supporters, reference numeral 105 denotes a gap or cavity, and reference numeral 106 denotes an insulating film on the chip 100. Reference numeral 107 denotes a conductive line connected to the first electrode 102, reference numeral 108 denotes a conductive line connected to the second electrode 103, reference numeral 109 denotes an external connection electrode connected to the conductive line 107, and reference numeral 110 denotes an external connection electrode connected to the conductive line 108. Reference numeral 120 denotes a flexible wire, reference numeral 121 denotes an external connection electrode, reference numeral 122 denotes a conductive layer, reference numeral 123 denotes a first insulating layer, reference numeral 124 denotes a second insulating layer, reference numeral 131 denotes a wire, reference numeral 140 denotes a supporting member, reference numeral 401 denotes an acoustic lens, reference numeral 402 denotes a silicone rubber layer, and reference numeral 500 denotes an electrostatic shield. The acoustic lens 401 is bonded to the electrostatic shield 500 via the silicone rubber layer 402. In the first embodiment, the electrostatic shield is at least arranged at a position opposed to the cells. The electrostatic shield is composed of a single electrostatic shield layer that has no opening and that is uniformly extended.

The chip 100 and the flexible wire 120 are arranged on the supporting member 140. In the first embodiment, a capacitive ultrasonic transducer (for example, a CMUT) is arranged on the chip 100 and is connected to a direct-current voltage generating unit 202 and a transmission-reception circuit 201 (refer to FIG. 1B) on the outside via the flexible wire 120. The vibrating membrane 101 is supported by the supporters 104 on the chip 100 and vibrates in response to the ultrasonic waves. The first electrode 102 is arranged on the vibrating membrane 101 and the second electrode 103 is arranged at a position on the chip 100, which is opposed to the first electrode 102. A set of the vibrating membrane 101, and the first electrode 102 and the second electrode 103, which are opposed to each other with the cavity 105 sandwiched therebetween, composes a cell.

As illustrated in FIG. 1B, the first electrode 102 is extended to the outside of the chip 100 via a first conductive line 301 and is connected to the transmission-reception circuit 201. The second electrode 103 is extended to the outside of the chip 100 via a second conductive line 302 and is connected to the direct-current voltage generating unit 202. Potential difference from several ten volts to several hundred volts is generated between the first electrode 102 and the second electrode 103 by the direct-current voltage generating unit 202. The vibration of the vibrating membrane 101 and the first electrode 102 varies the distance between the first electrode 102 and the second electrode 103 to vary the electrostatic capacitance between the electrodes. Since the potential difference exists between the electrodes, weak current occurs in response to the variation in capacitance. The weak current is converted into voltage in the transmission-reception circuit 201 connected to the first electrode 102 and the voltage is output from the transmission-reception circuit 201. The transmission is performed by vibrating the vibrating membrane 101 with alternating-current electrostatic attractive force caused between the first electrode 102 and the second electrode 103 in response to application of alternating-current drive voltage to the first electrode 102.

Multiple cells are arranged on the chip 100. In the first embodiment, the second electrodes 103 in the respective cells on the chip 100 are electrically connected to each other and have the same potential on the chip 100. In contrast, the first electrodes 102 on the chip 100 are electrically connected to each other in multiple groups and are electrically connected to the different transmission-reception circuits 201 for every group. Each group is referred to as an element in transmission and reception (for example, refer to an element 20 in FIG. 2). Typically, the transducer includes multiple elements each including at least one cell. The size (diameter) of each cell is several hundred micrometers to several millimeters and the number of the elements (the elements 20) is from one hundred to several thousands. The CMUT on the chip is capable of easily being manufactured using the MEMS technology. The chip 100 may be made of, for example, silicon or glass. In the first embodiment, each first electrode 102 is connected to the transmission-reception circuit 201 and it is necessary to electrically separate the first electrodes 102 for every element (element 20) in which the first electrodes 102 are connected to each other. However, since only changing the pattern of the uppermost electrode layer allows the first electrode and its conductive line to be formed, it is possible to manufacture the CMUT using a more simple method.

Figure 2:
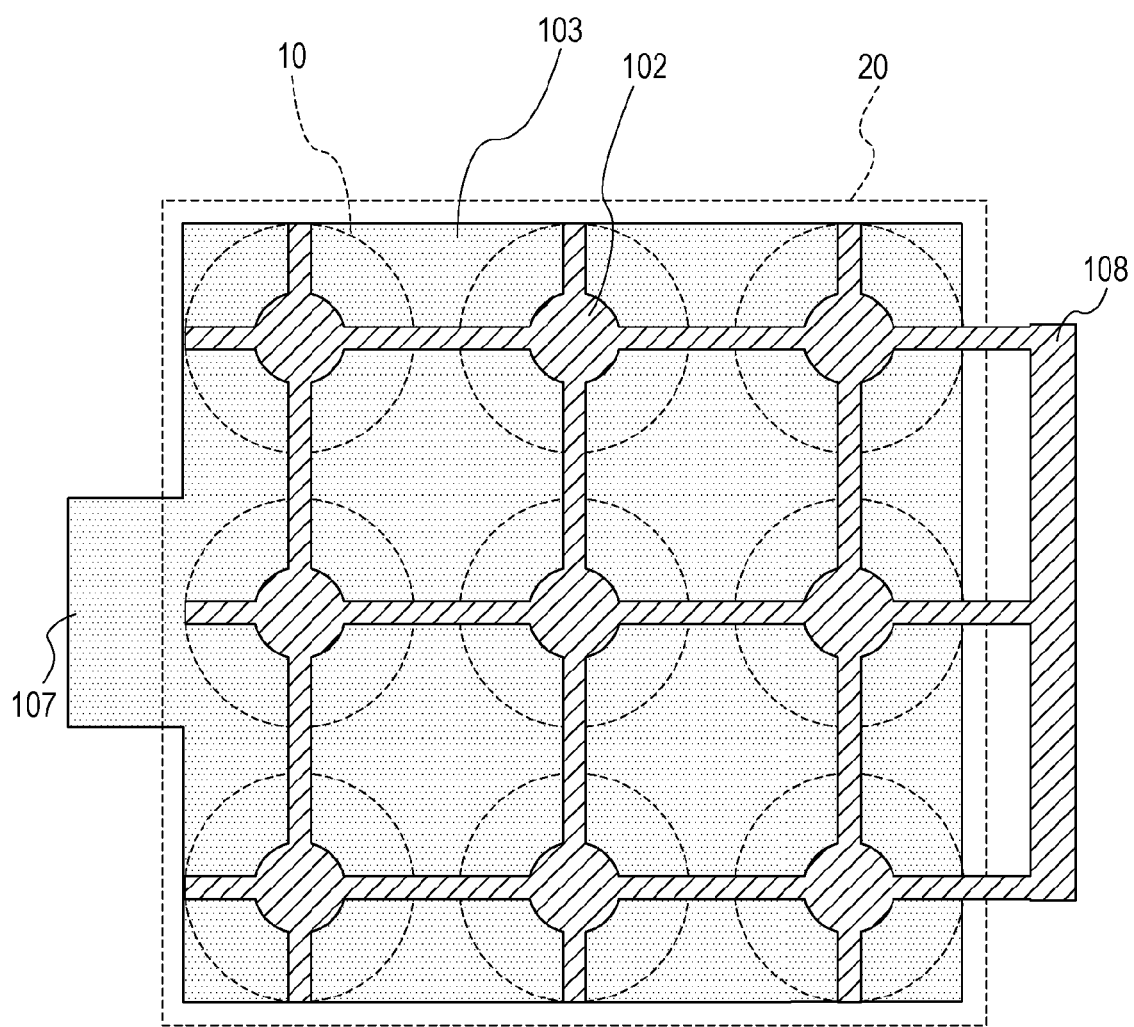
FIG. 2 is a top view for describing the capacitive transducer according to the first embodiment.

FIG. 2 is a schematic view for describing the shapes of the electrodes in the capacitive transducer of the first embodiment. The first electrode 102 on the vibrating membrane 101, the second electrode 103 on the surface of the chip 100, an outer shape of each cell 10, and an outer shape of the element 20 are illustrated in FIG. 2, which is a top view viewed from a sample 800 side (refer to FIG. 11 and FIG. 12). The second electrode 103 on the chip 100 is connected to the direct-current voltage generating unit 202 and is arranged over the surface of the chip 100.

Since noise in reception is increased if the first electrode 102 connected to the transmission-reception circuit 201 has a large parasitic capacitance, the area of the first electrode 102 is desirably small. In contrast, since the cell (the vibrating membrane 101) is most deformed in a central portion in the vibration of the vibrating membrane 101, only arranging each first electrode 102 only in the central portion of the cell allows reduction in the transmission efficiency and the reception sensitivity to be minimized. Accordingly, most of the area of the first electrode 102 is arranged in the central portion of the cell in the outer shape of the cell 10 and the first electrode 102 has a minimum width necessary for the connection between the first electrodes 102 in peripheral portions of the cell.

The flexible wire 120 arranged on the supporting member 140 with the chip 100 has a structure in which the thin conductive layer 122 is sandwiched between the two insulating layers 123 and 124. The conductive layer 122 is exposed from an end portion at the chip 100 side as the external connection electrode 121. As illustrated in FIG. 1A, the external connection electrodes 109 and 110 on the chip 100 are electrically connected to the external connection electrode 121 on the flexible wire 120 via the wire 131. The insulating layers of the flexible wire 120 are made of polyimide and the conductive layer of the flexible wire 120 is made of metal, such as copper or gold. The thickness of the entire flexible wire 120 is from several ten micrometers to one hundred micrometers.

The acoustic lens 401 is arranged on the chip 100 and the flexible wire 120, which are arranged on the supporting member 140, via the silicone rubber layer 402 in the first embodiment. One electrostatic shield 500 is arranged in the silicone rubber layer 402. The silicone rubber layer 402 is mainly used to bond the acoustic lens 401 to the chip 100. When common adhesive is used, for example, reflection may occur on the interface and/or vibration characteristics of the vibrating membrane may be affected by the hard adhesive because the acoustic impedance of the adhesive is different from the acoustic impedance of portions in contact with the silicone rubber layer. Accordingly, the bonding using the silicone rubber layer is essential or preferred. The silicone rubber layer may incidentally protect the surface of the transducer and ensure the insulation. In the embodiments of the present invention, the silicone rubber layer may be made of rubber containing polydimethylsiloxane (PDMS). Since the silicone rubber has a low Young's modulus (stiffness), the mechanical characteristics of the vibrating membrane are less affected by the silicone rubber.

The electrostatic shield 500 of the first embodiment is formed of a metal thin-film layer, is set so as to have fixed potential equal to reference voltage Vref of the transmission-reception circuit 201, and has characteristics in which the ultrasonic waves are transmitted through the electrostatic shield 500 without deterioration. The electrostatic shield 500 may be made of, for example, aluminum, copper, nickel, or gold and is set so as to have a thickness sufficiently smaller than the wavelength of the ultrasonic waves that are used. It is sufficient for the electrostatic shield 500 to have the material and the thickness that ensure the transmission characteristics of the ultrasonic waves and a sufficiently low electrical resistance. In particular, the electrostatic shield having a thickness of several micrometers or less is desirably used. In contrast, the silicone rubber layer 402 that has no effect on the transmission and reception characteristics of the vibrating membrane 101 of the transducer and that enables the bonding between the acoustic lens 401 and the chip 100 is desirably used, as described above. In addition, the silicone rubber layer 402 is desirably made of a material consistent with the acoustic impedances of a living body, which is a sample, and the acoustic lens 401. The silicone rubber layer 402 is desirably capable of minimizing the reflection of the ultrasonic waves from the interface between the acoustic lens 401 and the silicone rubber layer 402.

When the transducer is used in contact with the sample information acquisition apparatus, the transducer may be used in a state in which a sample, such as a living body, is arranged near the surface of the acoustic lens 401. Gel (ultrasound gel) is generally filled between the acoustic lens 401 and the sample so that the transmission characteristics of the ultrasonic waves are not deteriorated because of a bubble or the like. The surface of the sample is charged and may be greatly charged depending on the surface state. The transmission and reception characteristics of the transducer may be greatly affected by the charge of the surface of the sample. The inventor has found that there is a problem in that, when the capacitive transducer (the CMUT or the like) is used in contact with a sample, such as a living body, the transmission and reception characteristics of the transducer are affected by the electric charge existing on the surface of the sample to deteriorate the transmission and reception characteristics. In the configuration in the related art in which the electrostatic shield is not provided, when a sample with the charged surface comes close to the transducer, electrostatic coupling may occur between the sample and the first electrode 102, the electric charge may be induced to the first electrode 102, and noise may be generated in the reception. Simultaneously, the line of electric force between the first electrode 102 and the second electrode 103 may be varied to vary the strength of the electric field between the first electrode 102 and the second electrode 103. As a result, the transmission efficiency of the output sound pressure in the transmission and the reception sensitivity of the sound pressure in the reception are varied. Such effects from the sample are liable to occur when the distance between the sample and the first electrode 102 is short.

In contrast, in the first embodiment, the electrostatic shield 500 is provided. Accordingly, even if the sample with the charged surface comes close to the transducer, the electric charge induced from the sample 800 occurs in the electrostatic shield 500 and almost no electric charge occurs in the first electrode 102 on the chip 100. Since the first electrode 102 of the first embodiment is surrounded by the second electrode 103 having the fixed potential and the electrostatic shield 500, the shape of the line of electric force between the first electrode 102 and the second electrode 103 is hardly varied due to the sample 800 outside the second electrode 103 and the electrostatic shield 500. Accordingly, in the first embodiment, the transmission efficiency of the output sound pressure in the transmission and the reception sensitivity of the sound pressure in the reception are hardly varied by the sample. As described above, according to the first embodiment, since the transmission and reception characteristics are less affected by the electric charge of the sample on the surface of the transducer, it is possible to provide the capacitive transducer having excellent transmission and reception characteristics.

In addition, in the first embodiment, the direct-current high voltage is applied to the second electrode 103 and the second electrode 103 is covered with the first electrode 102 the voltage of which is generally fixed to a value near the reference voltage of the transmission-reception circuit 201. Accordingly, since the electrode to which the direct-current high voltage is applied is arranged at a position more apart from the sample, it is possible to increase the insulation from the sample to provide the transducer with high safety.

<Second Embodiment>

Figure 3:
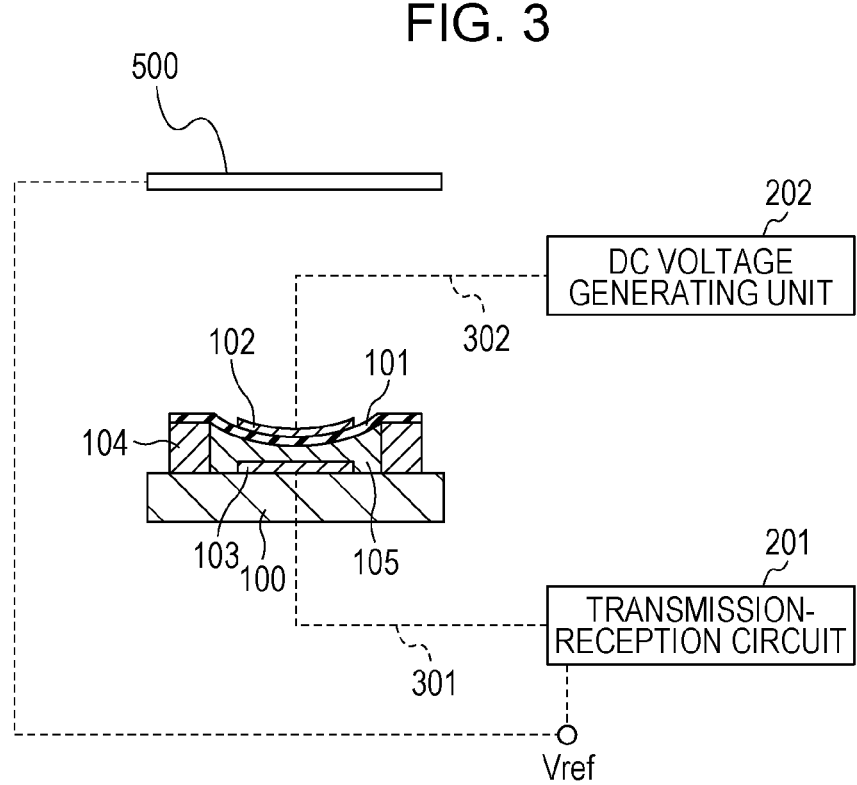
FIG. 3 is a cross-sectional view for describing a capacitive transducer according to a second embodiment.

A second embodiment differs from the first embodiment in the configuration of electrodes in a capacitive transducer. The second embodiment is the same as the first embodiment in the other points. FIG. 3 is a schematic cross-sectional view for describing a capacitive transducer according to the second embodiment. As illustrated in FIG. 3, the second embodiment is characterized in that the direct-current voltage generating unit 202 is connected to the first electrode 102 and the transmission-reception circuit 201 is connected to the second electrode 103.

The line of electric force between the first electrode 102 and the second electrode 103 when the electrostatic shield 500 is not provided will now be considered. As described above in the first embodiment, the first electrode 102 has a pattern and has a surface area smaller than that of the second electrode 103 (refer to FIG. 2). Accordingly, the line of electric force between the first electrode 102 and the second electrode 103 has a shape extended toward the second electrode 103. Accordingly, when the charged sample exists on the first electrode 102, the shape of the line of electric force is affected and is liable to be deformed. The variation in the shape of the line of electric force varies the transmission efficiency of the output sound pressure in the transmission and the reception sensitivity of the sound pressure in the reception. Accordingly, the transmission and reception characteristics of the capacitive transducer, such as the CMUT, are varied depending on the surface state of the sample to lead deterioration of the performance as the transducer. The effect from the sample is liable to occur when the distance between the second electrode 103 connected to the transmission-reception circuit 201 and the sample is short.

However, since the electrostatic shield 500 is provided between the sample and the transducer in the second embodiment, the line of electric force between the first electrode 102 and the second electrode 103 is less affected by the surface state of the sample and the variation in the transmission and reception characteristics is suppressed. In addition, since the second electrode 103 connected to the transmission-reception circuit 201 is relatively apart from the sample, the second electrode 103 is less affected by the sample.

<Third Embodiment>

Figure 4:
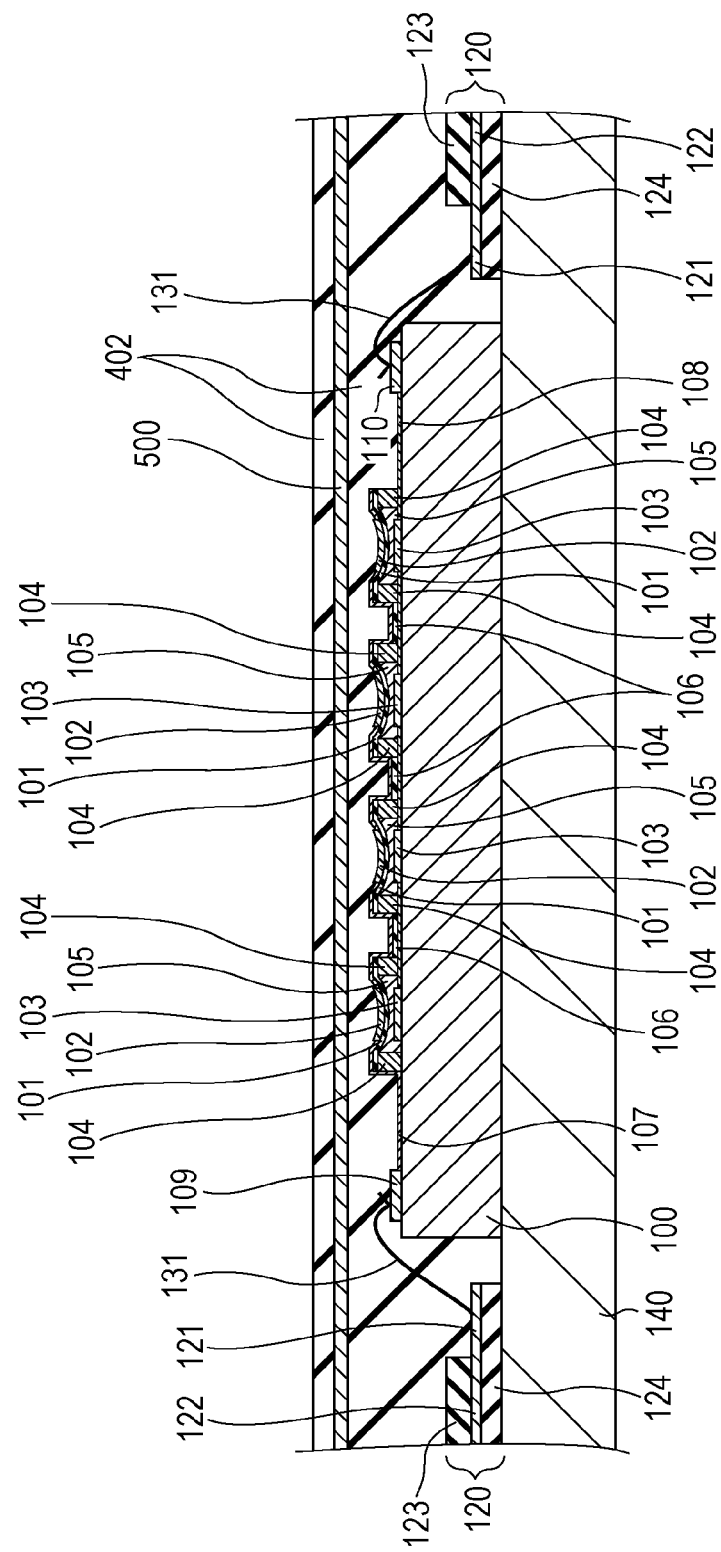
FIG. 4 is a cross-sectional view for describing a capacitive transducer according to a third embodiment.

A third embodiment differs from the above embodiments in the components arranged on the surface of the transducer. The third embodiment is the same as the first and second embodiments in the other points. FIG. 4 is a schematic cross-sectional view for describing a capacitive transducer according to the third embodiment.

The capacitive transducer of the third embodiment has a configuration in which the acoustic lens 401 is not provided. The transducer having no acoustic lens is preferably used as a transmission-reception transducer that performs electronic focusing or a photoacoustic transducer that receives ultrasonic waves (photoacoustic waves) caused by a photoacoustic effect.

In the configuration of the third embodiment, the acoustic lens 401 generally having a thickness of several hundred micrometers to several millimeters is not provided and the sample 800 is in contact with the surface of the transducer via the silicone rubber layer 402 having a thickness of several ten micrometers to one hundred micrometers. Accordingly, the distance between the sample 800 and the electrodes in the transducer is greatly decreased, compared with the case in which the acoustic lens 401 is provided, and the transducer is liable to be greatly affected from the surface of the sample 800. However, since the electrostatic shield 500 is provided between the sample 800 and the electrodes in the transducer also in the third embodiment, the deterioration in the transmission and reception characteristics hardly occurs also in the configuration in which the distance between the sample 800 and the electrodes in the transducer is very short. Accordingly, it is possible to provide the capacitive transducer the transmission and reception characteristics of which are less affected by the surface state of the sample also in the configuration in which the acoustic lens 401 is not provided.

Figure 5:
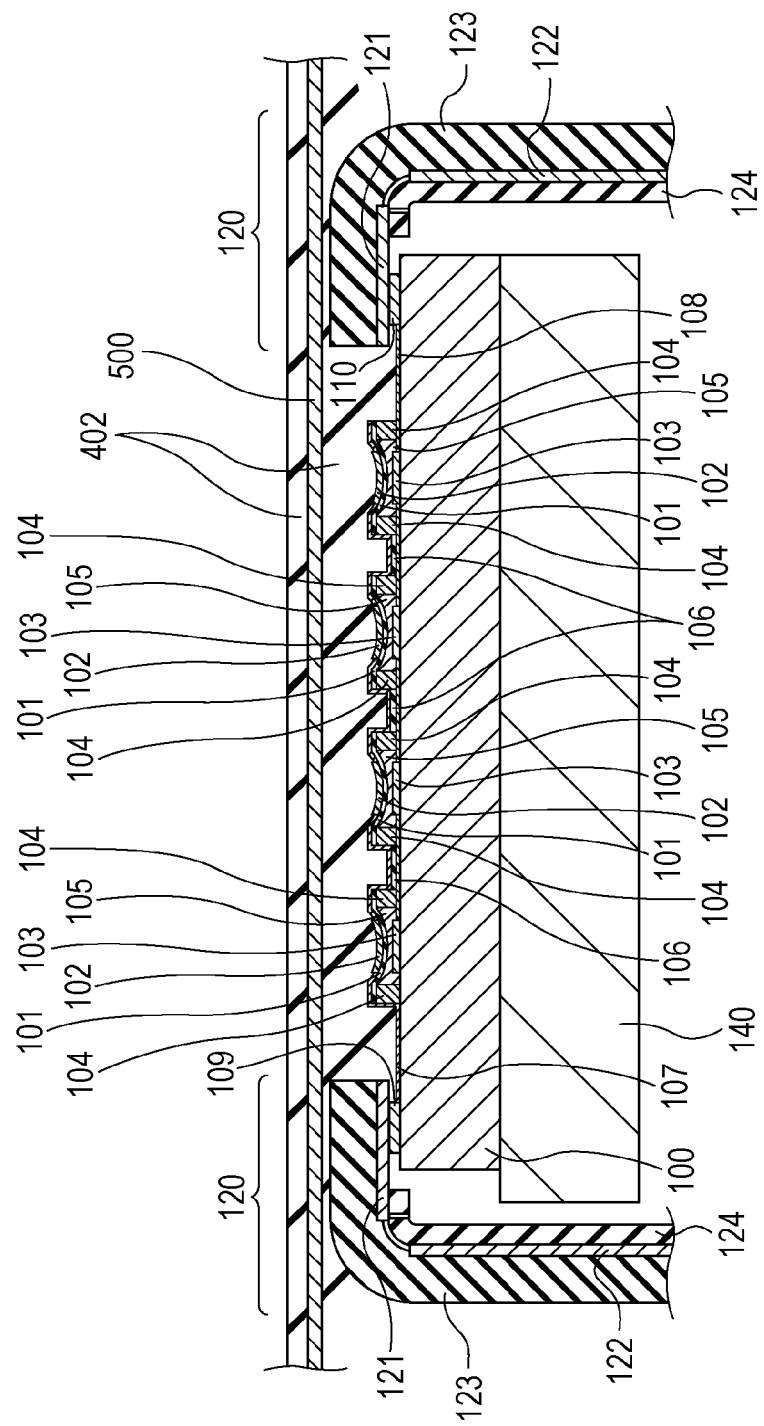
FIG. 5 is a diagram for describing another example of the third embodiment.

Modifications of the third embodiment will now be described with reference to FIG. 5 and FIG. 6. FIG. 5 illustrates an exemplary capacitive transducer that differs from the above embodiments in the connection state between the chip 100 and the flexible wire 120, which connects the electrodes on the chip 100 to the direct-current voltage generating unit 202 and the transmission-reception circuit 201 outside the transducer. Referring to FIG. 5, the flexible wire 120 is arranged so as to be opposed to the external connection electrodes 109 and 110 on the chip 100 for electrical connection. Specifically, the flexible wire electrically connected to the external connection electrodes is provided so as to be opposed to the face of the chip on which the cells are provided. The external connection electrodes 109 and 110 on the chip 100 are capable of easily being connected to the external connection electrode 121 in the flexible wire 120 using, for example, anisotropic conductive film (ACF). With the connection method illustrated in FIG. 5, the height of the protrusions on the surface of the chip 100 is decreased, compared with the case illustrated in FIG. 4 in which the wire 131 is used. Accordingly, the thickness of the silicone rubber layer 402 on the chip 100 may be decreased. Since attenuation of the ultrasonic waves occurs in the silicone rubber layer 402, the transmission and reception characteristics are improved with the decreasing thickness of the silicone rubber layer 402. In contrast, the transmission and reception characteristics are more liable to be affected by the surface state of the sample with the decreasing thickness of the silicone rubber layer 402. However, since the use of the configuration of the third embodiment including the electrostatic shield 500 causes the transducer to be less affected by the sample, the excellent transmission and reception characteristics are kept.

As described above, in the modification illustrated in FIG. 5, it is possible to realize the capacitive transducer that has the excellent transmission and reception characteristics and that are less affected by the surface state of the sample also in the configuration in which the acoustic lens 401 is not provided.

Figure 6:
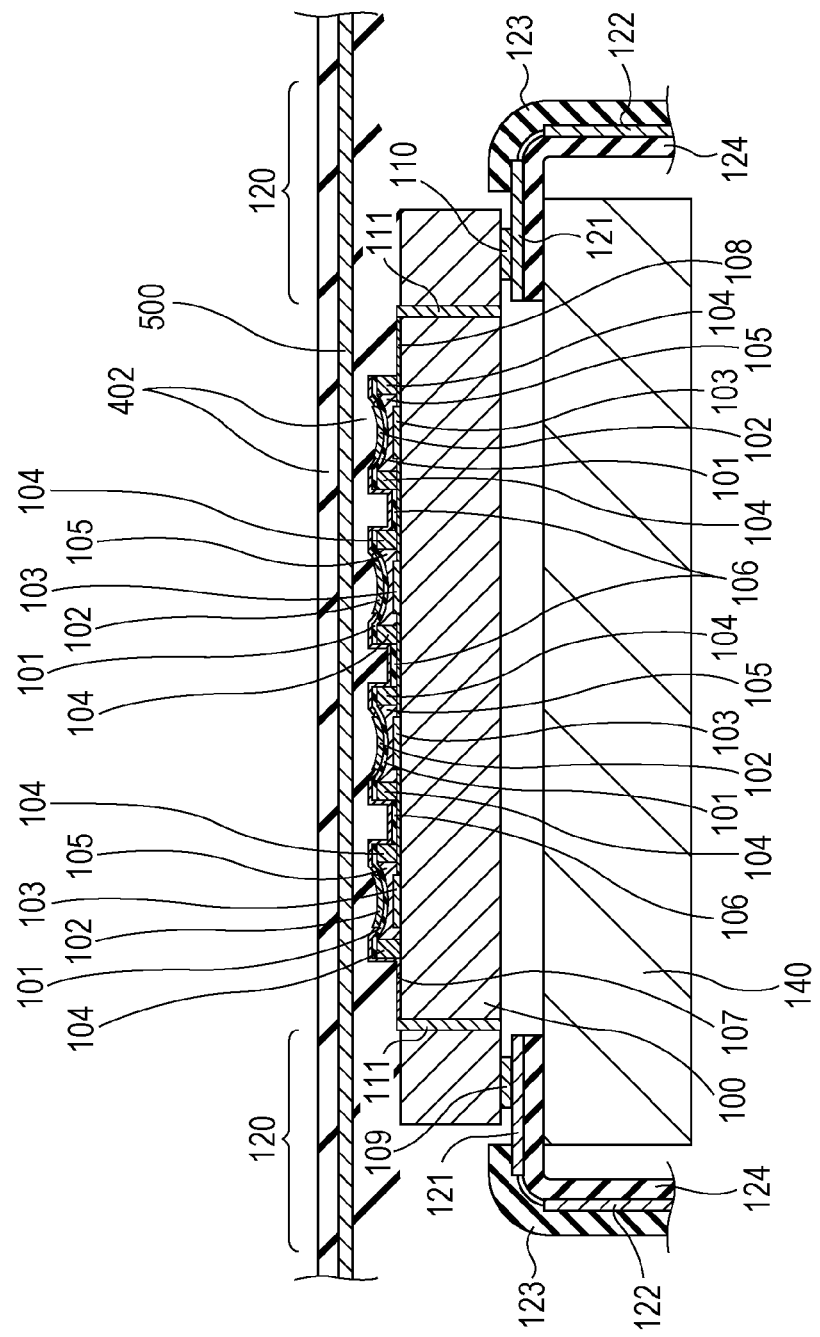
FIG. 6 is a diagram for describing another example of the third embodiment.

FIG. 6 illustrates another exemplary capacitive transducer that differs from the above embodiments in the connection state between the chip 100 and the flexible wire 120, which connects the electrodes on the chip 100 to the direct-current voltage generating unit 202 and the transmission-reception circuit 201 outside the transducer. The configuration in FIG. 6 differs from the configuration in FIG. 5 in that the external connection electrodes 109 and 110 on the chip 100, which are electrically connected to the flexible wire 120, are arranged on a face (rear face) opposite to the face of the chip 100 on which the cells are formed. Specifically, the flexible wire electrically connected to the external connection electrodes is provided so as to be opposed to the face opposite to the face of the chip on which the cells are provided. In the configuration in FIG. 6, the chip 100 includes a thorough line 111 for the electrical connection to the flexible wire 120 on the rear face of the chip 100. With the connection method illustrated in FIG. 6, the protrusions are not provided on the surface of the chip 100. Accordingly, it is possible to decrease the thickness of the silicone rubber layer 402 on the chip 100 to a thickness that achieves the most excellent transmission and reception characteristics. In the modification illustrated in FIG. 6, it is possible to provide the capacitive transducer that has the especially excellent transmission and reception characteristics and that are less affected by the surface state of the sample also in the configuration in which the acoustic lens 401 is not provided.

<Fourth Embodiment>

Figure 7:
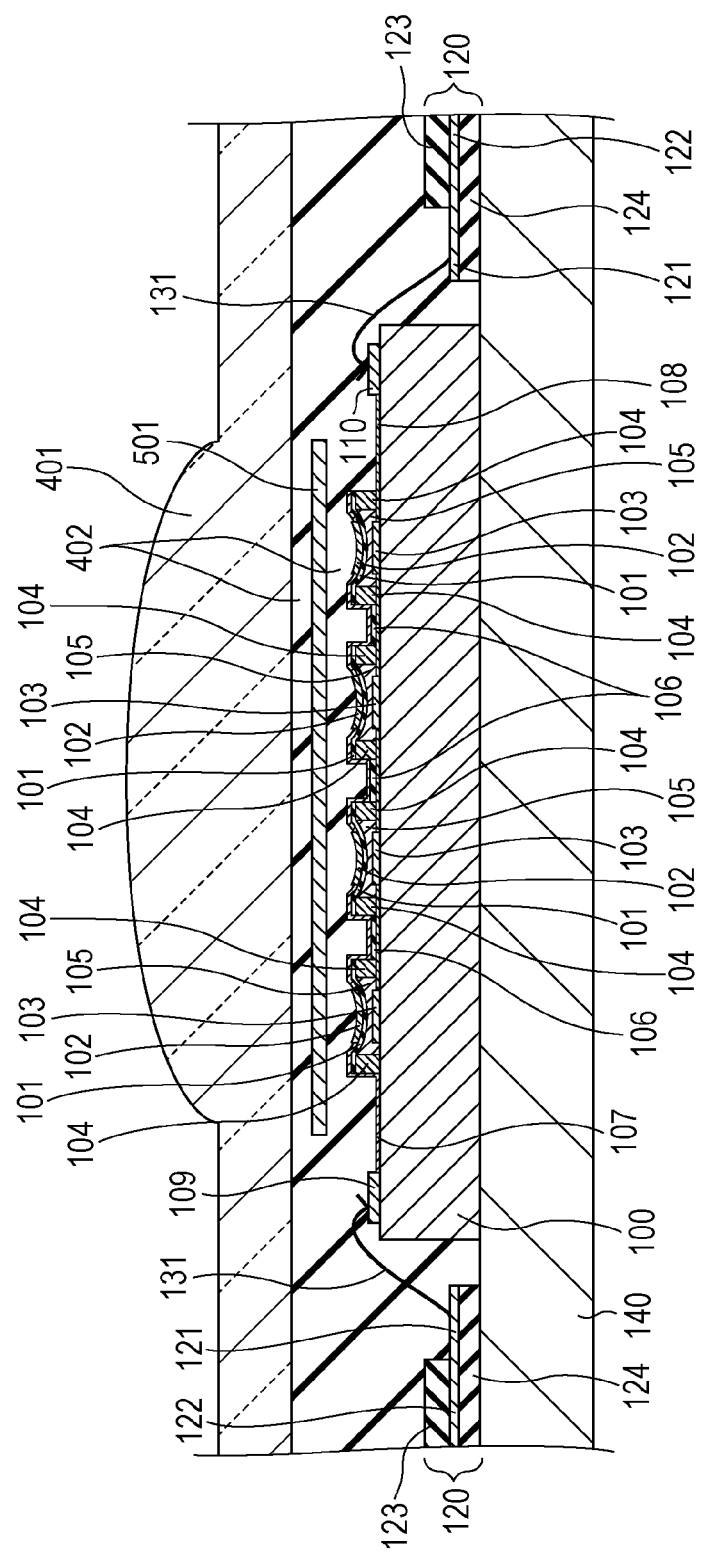
FIG. 7 is a cross-sectional view for describing a capacitive transducer according to a fourth embodiment.

A fourth embodiment differs from the above embodiments in an area where the electrostatic shield is arranged. The fourth embodiment is the same as any of the first to third embodiments in the other points. FIG. 7 is a schematic cross-sectional view for describing a capacitive transducer according to the fourth embodiment.

The fourth embodiment is characterized in that an electrostatic shield 501 is arranged in an area opposed to the area on the chip 100 where the first electrodes 102 and the second electrodes 103 are arranged. In the fourth embodiment, the arrangement of the electrostatic shield 501 only in the area opposed to the area where the cells are arranged allows the configuration to be simplified, compared with the case in which the electrostatic shield is entirely arranged. In addition, the transducer is manufactured by arranging the cells on the chip 100, arranging the electrostatic shield 501, and electrically connecting the chip to the flexible wire 120. Accordingly, since the restriction on the manufacturing method is small, it is possible to manufacture the transducer using the easier manufacturing method.

<Fifth Embodiment>

Figure 8B:
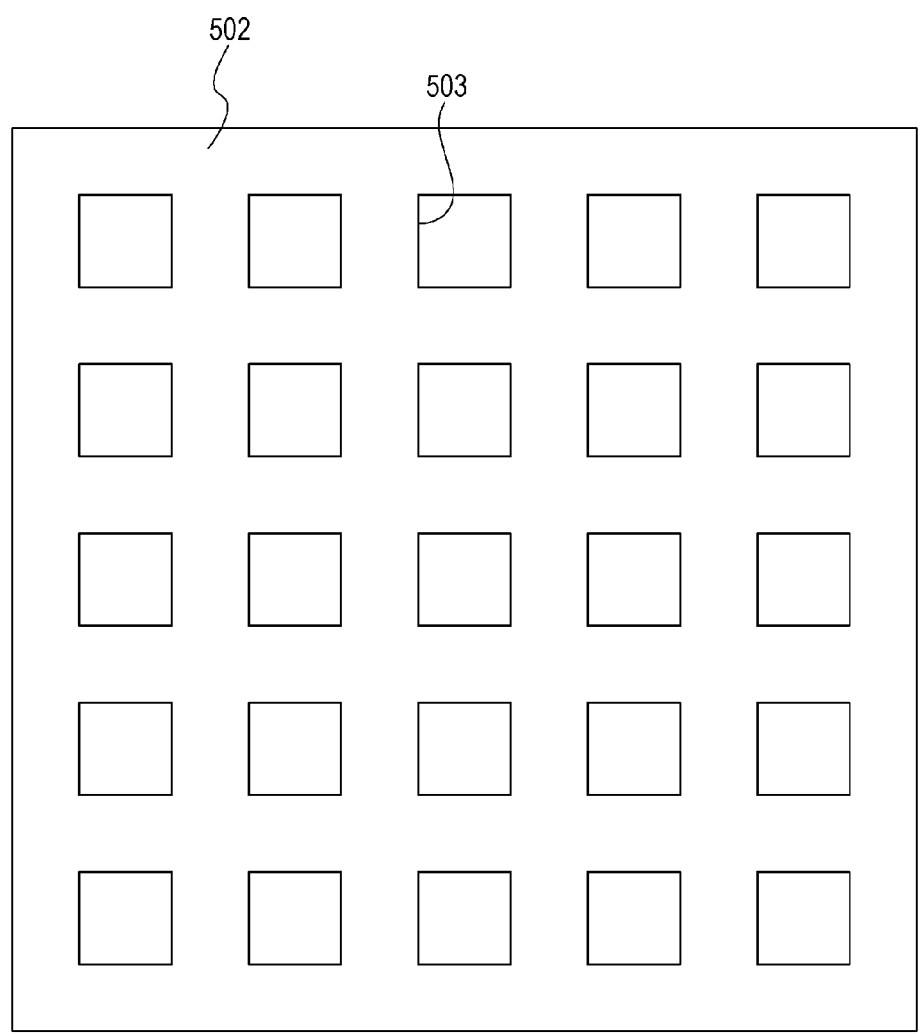
FIG. 8B is a top view for describing an electrostatic shield of the fifth embodiment.

A fifth embodiment differs from the above embodiments in the shape of an electrostatic shield 502. The fifth embodiment is the same as any of the first to fourth embodiments in the other points. FIGS. 8A to 8E are diagrams for describing a capacitive transducer according to the fifth embodiment. FIG. 8A is a schematic cross-sectional view of the capacitive transducer. FIG. 8B is a schematic view when the electrostatic shield is viewed from above.

The electrostatic shield 502 of the fifth embodiment is characterized in that multiple openings 503 are two-dimensionally arranged periodically, as illustrated in FIG. 8B. In other words, the electrostatic shield has the multiple openings when the electrostatic shield is viewed from above the cells. Since the size of the openings 503 is sufficiently smaller than the surface area of the sample 800, the shielding effect is hardly reduced even when the electrostatic shield 502 has the multiple openings 503. The size and the arrangement cycle of the openings 503 may be set to arbitrary values as long as the transmission and reception characteristics are not affected by the sample via the electrodes on the chip 100. Although the multiple openings 503 are opposed to the multiple cells in an irregular pattern in the configuration in FIG. 8A, the arrangement is not limited to this.

Small parasitic capacitance occurs between the electrostatic shield 502 and the first electrode 102 (or the second electrode 103) on the chip 100. The parasitic capacitance is increased in size with the decreasing distance between the electrostatic shield 502 and the first electrode 102 (or the second electrode 103) on the chip 100. The parasitic capacitance at the electrodes connected to the transmission-reception circuit 201 causes a reduction in the reception sensitivity and an increase in the output noise in the reception. Against such a situation, in the electrostatic shield 502 including the openings 503 in the fifth embodiment, the surface area of the electrostatic shield 502 is capable of being decreased in response to an increase in the total area of the openings 503. Accordingly, the magnitude of the parasitic capacitance occurring between the electrostatic shield 502 and the first electrode 102 (or the second electrode 103) on the chip 100 is capable of being suppressed while the effect of the electrostatic shield is being kept. In particular, when the effects on the reception characteristics, such as a reduction in the reception sensitivity and an increase in the output noise, are undesirably caused, the use of the electrostatic shield of the fifth embodiment reduces the effects on the reception characteristics.

As described above, according to the fifth embodiment, it is possible to realize the capacitive transducer in which the undesirable effects on the reception characteristics, such as a reduction in the reception sensitivity and an increase in the output noise, are reduced and which is less affected by the surface state of the sample.

Figure 8C:
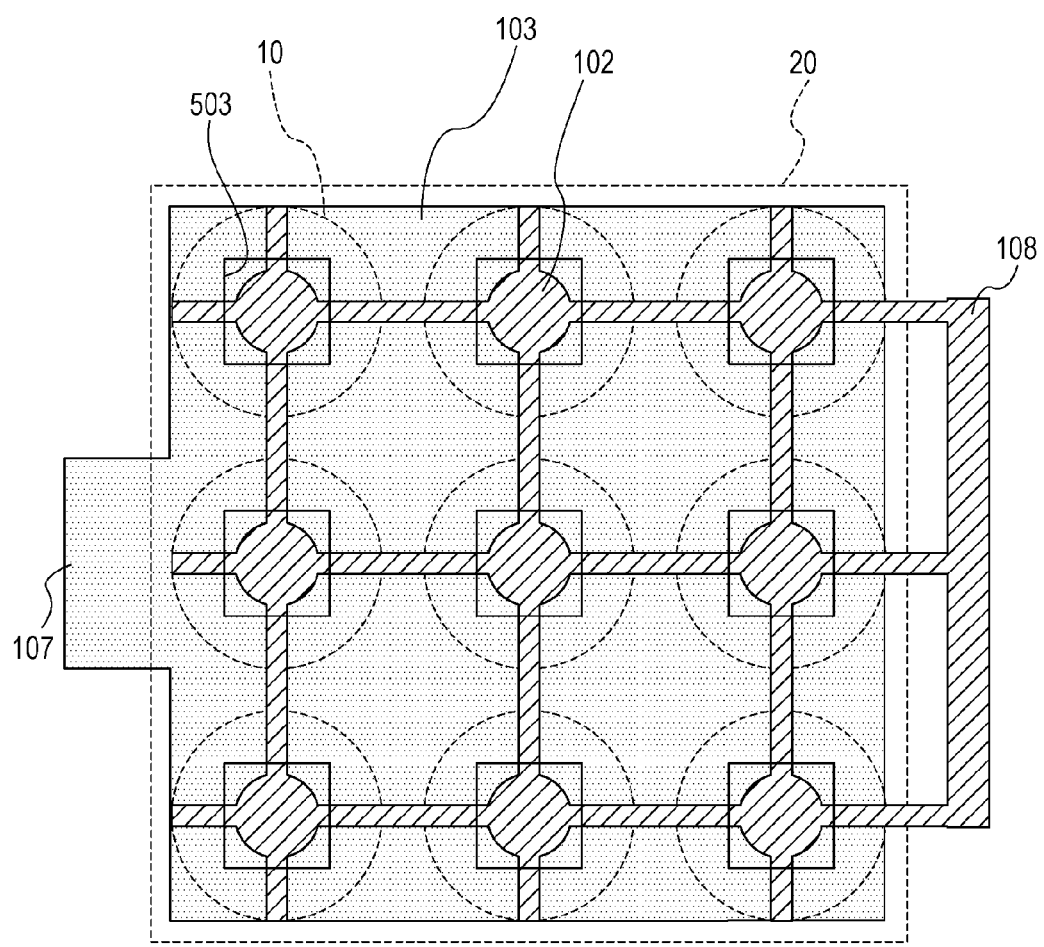
FIG. 8C is a top view for describing an example of the arrangement of the electrostatic shield of the fifth embodiment.

A modification of the fifth embodiment will now be described with reference to FIG. 8C. FIG. 8C is a schematic view when the electrostatic shield is viewed from the top face of the chip 100 (the face on which the cells are arranged). Only the relationship between the first electrode 102 on the vibrating membrane 101, the second electrode 103 on the chip 100, and the outer shapes of the cells 10 is illustrated in FIG. 8C. The configuration in FIG. 8C is characterized in that each of the openings 503 of the electrostatic shield 502 is arranged at a position corresponding to a central portion of the cell. In other words, the multiple openings of the electrostatic shield are regularly arranged at the positions corresponding to the cells. In the configuration in FIG. 8C, the first electrode 102 is connected to the transmission-reception circuit 201, as in the configuration in the first embodiment. Since the area of the first electrode 102 is largest around the central portion of the cell, the arrangement of each of the openings 503 of the electrostatic shield 502 at the position opposed to the central portion of the cell allows the magnitude of the parasitic capacitance between the first electrode 102 and the electrostatic shield 502 to be further decreased.

With the configuration illustrated in FIG. 8C, it is possible to realize the capacitive transducer in which the undesirable effects on the reception characteristics, such as a reduction in the reception sensitivity and an increase in the output noise, are further reduced and which is less affected by the surface state of the sample.

Figure 8D:
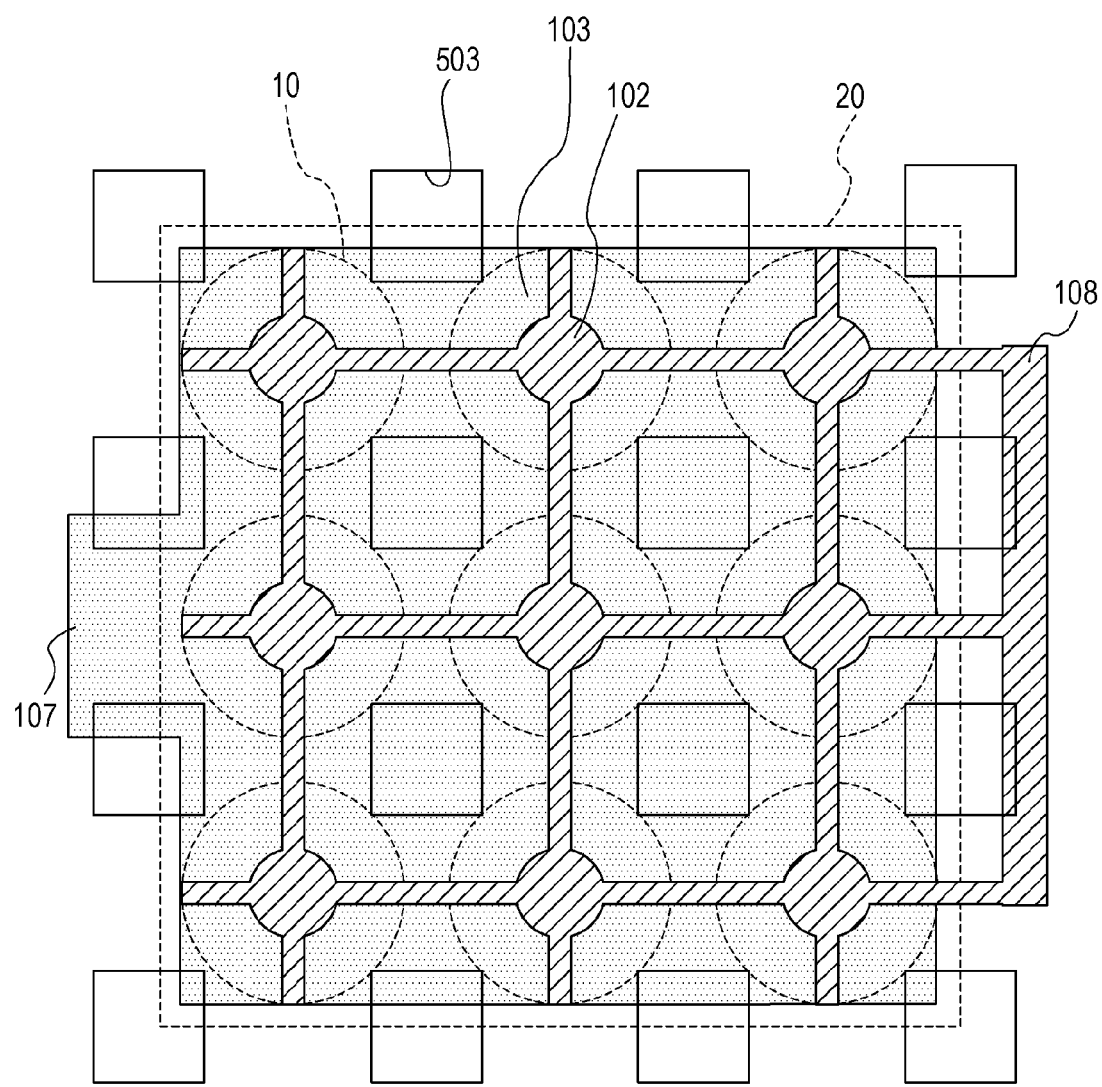
FIG. 8D is a top view for describing another example of the arrangement of the electrostatic shield of the fifth embodiment.

Another modification of the fifth embodiment will now be described with reference to FIG. 8D. FIG. 8D is a schematic view when the electrostatic shield is viewed from the top face of the chip 100 (the face on which the cells are arranged). Only the relationship between the first electrode 102, the second electrode 103, and the outer shapes of the cells 10 is illustrated also in FIG. 8D. The configuration in FIG. 8D is characterized in that each of the openings 503 of the electrostatic shield 502 is shifted from the position corresponding to the central portion of the cell 10 as much as possible. In other words, the multiple openings of the electrostatic shield are arranged at the positions corresponding to areas shifted from the cells. In the configuration in FIG. 8D, the second electrode 103 is connected to the transmission-reception circuit 201, as in the configuration in the second embodiment (refer to FIG. 3). The second electrode 103 is covered with the first electrode 102 having the pattern near the central portion of the cell. In contrast, the second electrode 103 is not almost covered with the first electrode 102 in an area apart from the central portion of the cell. Accordingly, the shift of each of the openings 503 of the electrostatic shield 502 from the position corresponding to the central portion of the cell as much as possible allows the magnitude of the parasitic capacitance between the second electrode 103 connected to the transmission-reception circuit 201 and the electrostatic shield 502 to be further decreased. Since the effect of the electrostatic shield 502 is little varied depending on the positions of the openings 503, the capacitive transducer is hardly affected by the surface state of the sample.

Figure 8E:
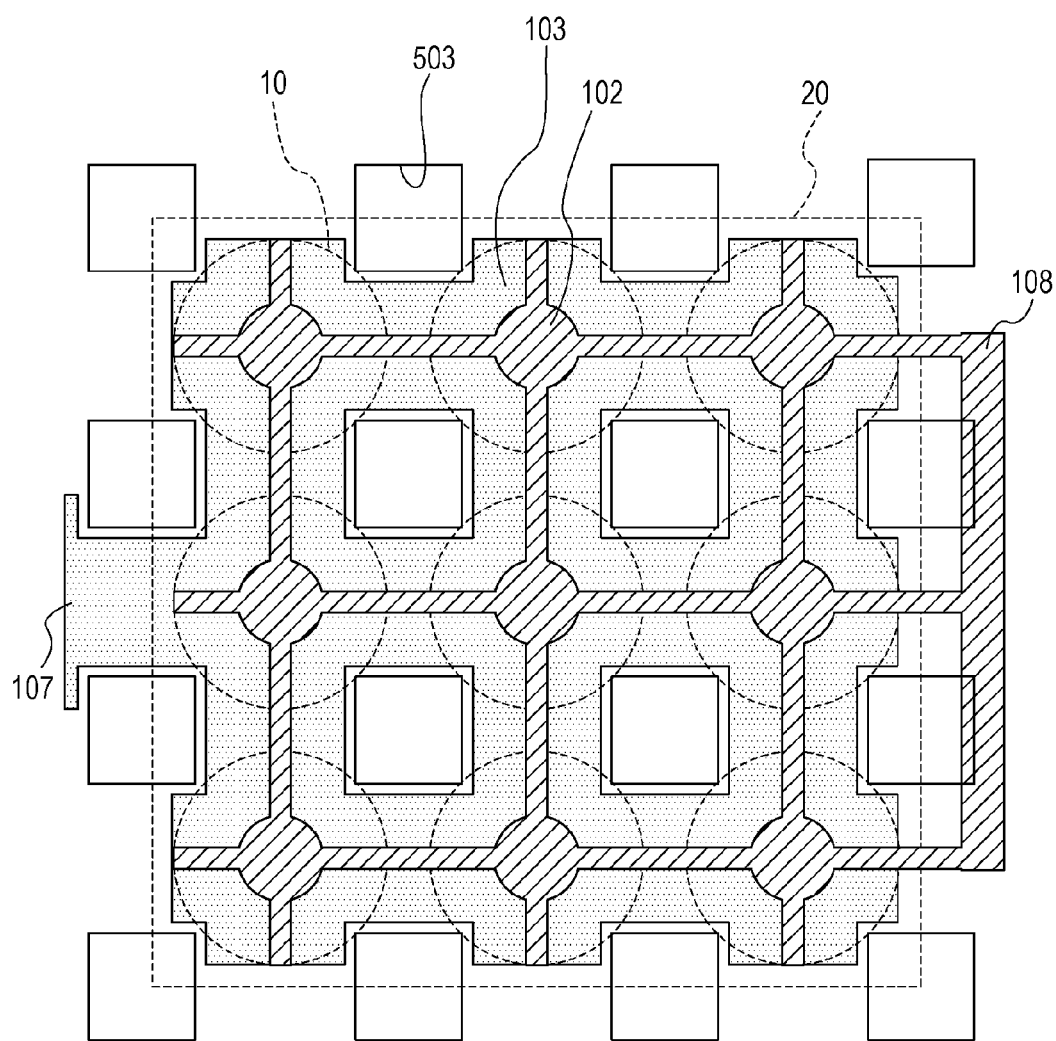
FIG. 8E is a top view for describing another example of the fifth embodiment.

As illustrated in FIG. 8E, the second electrode 103 may be configured so as to have a pattern in which no electrode is provided in areas opposed to the openings 503 of the electrostatic shield 502. This configuration allows an occurrence of the parasitic capacitance to be further suppressed. Accordingly, it is possible to provide the capacitive transducer having more excellent reception characteristics. With the configurations illustrated in FIG. 8D and FIG. 8E, it is possible to realize the capacitive transducers in which the undesirable effects on the reception characteristics, such as a reduction in the reception sensitivity and an increase in the output noise, are further reduced and which are less affected by the surface state of the sample.

<Sixth Embodiment>

Figure 9A:
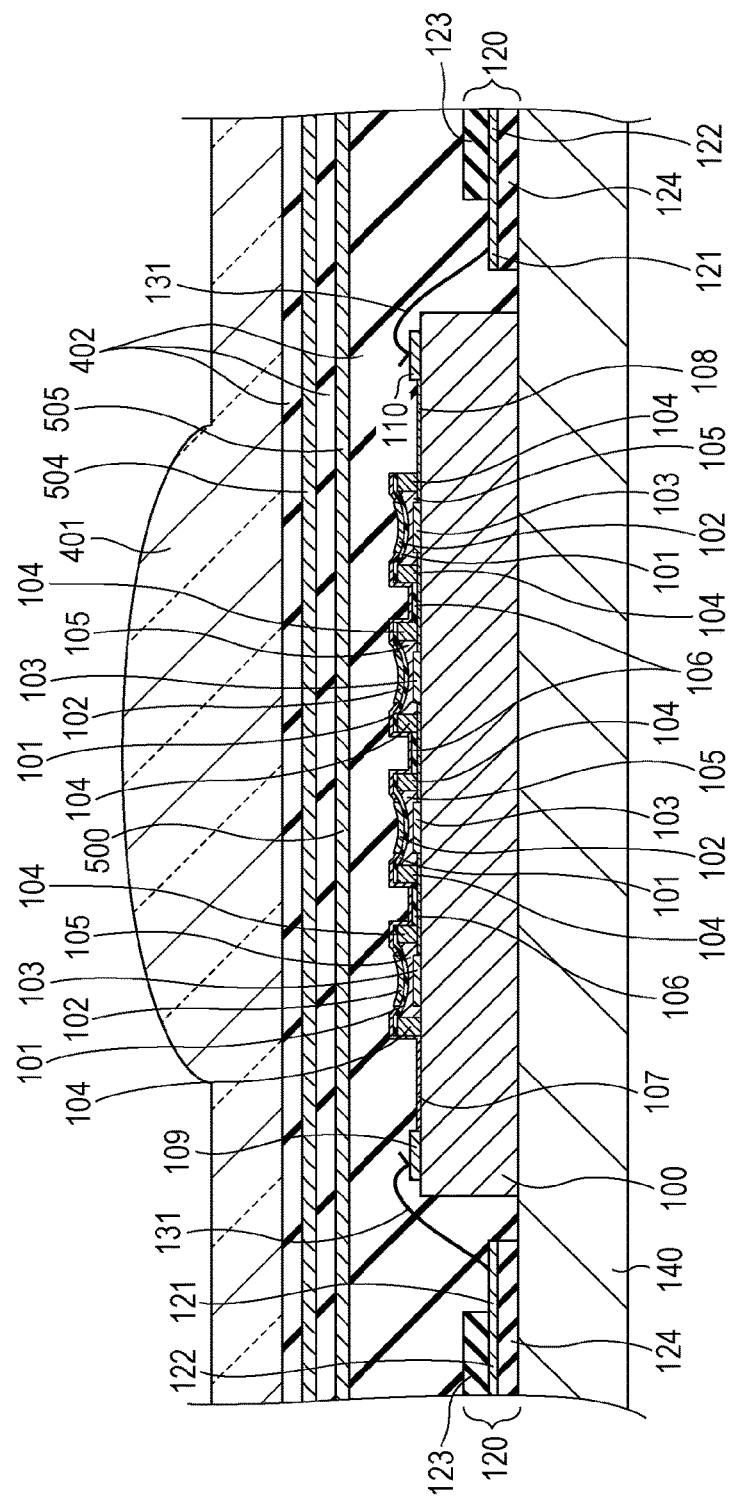
FIG. 9A is a cross-sectional view for describing a capacitive transducer according to a sixth embodiment.

A sixth embodiment differs from the above embodiments in the shape of the electrostatic shield 500. The sixth embodiment is the same as any of the first to fifth embodiments in the other points. FIGS. 9A to 9C are diagrams for describing a capacitive transducer according to the sixth embodiment. The sixth embodiment is characterized in that the electrostatic shield 500 is composed of multiple electrostatic shield layers. The multiple layers are set so as to have to the same fixed potential.

In the sixth embodiment, two electrostatic shield layers 504 and 505 are used, as illustrated in FIG. 9A, which is a schematic cross-sectional view. The electrostatic shield layers 504 and 505 are arranged at different heights. FIG. 9B is a top view for describing the first electrostatic shield layer 504 and the second electrostatic shield layer 505. In the first electrostatic shield layer 504, the electrodes are arranged so as to draw vertical stripes on the plane of paper. In contrast, in the second electrostatic shield layer 505, the electrodes are arranged so as to draw vertical stripes slightly shifted from the vertical stripes of the first electrostatic shield layer 504 on the plane of paper. No gap exists when the first electrostatic shield layer 504 is deposited on the second electrostatic shield layer 505 and the first electrostatic shield layer 504 and the second electrostatic shield layer 505 are viewed from above.

Since the electrostatic shield is divided into the multiple layers in the sixth embodiment, the effective distance between the first electrode 102 (or the second electrode 103) on the chip 100 and the electrostatic shield 500 is increased, compared with the case in which the electrostatic shield is composed of one layer. Accordingly, the magnitude of the parasitic capacitance occurring between the first electrode 102 (or the second electrode 103) and the electrostatic shield 500 is further reduced.

With the configuration illustrated in FIG. 9A and FIG. 9B, it is possible to provide the capacitive transducer in which the undesirable effects on the reception characteristics, such as a reduction in the reception sensitivity and an increase in the output noise, are further reduced and which is less affected by the surface state of the sample.

A modification of the sixth embodiment will now be described with reference to FIG. 9C. In the modification in FIG. 9C, the first electrostatic shield layer 504 has the electrodes arranged so as to draw vertical stripes, as in FIG. 9B. The second electrostatic shield layer 505 has the electrodes arranged so as to draw horizontal stripes. The configuration in FIG. 9C differs from the configuration in FIG. 9B in that, when the first electrostatic shield layer 504 is deposited on the second electrostatic shield layer 505, openings are periodically formed. The arrangement of the openings may be varied by appropriately designing the vertical and horizontal strip patterns and the manner in which the shield layers are deposited.

With the configuration illustrated in FIG. 9C, the effective distance between the first electrode 102 (or the second electrode 103) on the chip 100 and the electrostatic shield 500 is increased and the magnitude of the parasitic capacitance is greatly reduced due to the presence of the openings. With the configuration illustrated in FIG. 9C, it is possible to provide the capacitive transducer in which the undesirable effects on the reception characteristics, such as a reduction in the reception sensitivity and an increase in the output noise, are further reduced and which is less affected by the surface state of the sample.

Although the electrostatic shield is composed of the two layers in the sixth embodiment described above, the sixth embodiment is not limited to the above configurations and may have a configuration in which three or more shield layers are used. In addition, the shield layers may have no pattern (that is, the electrostatic shield layers having no opening). The shield layers of such configurations have the advantages in that a problem involved in the stress or the like, which may occur in the formation of the thick shield layers, is avoided and in that the multiple thin shield layers having slightly high resistance are arranged to reduce the entire resistance of the shield layers.

<Seventh Embodiment>

Figure 10B:
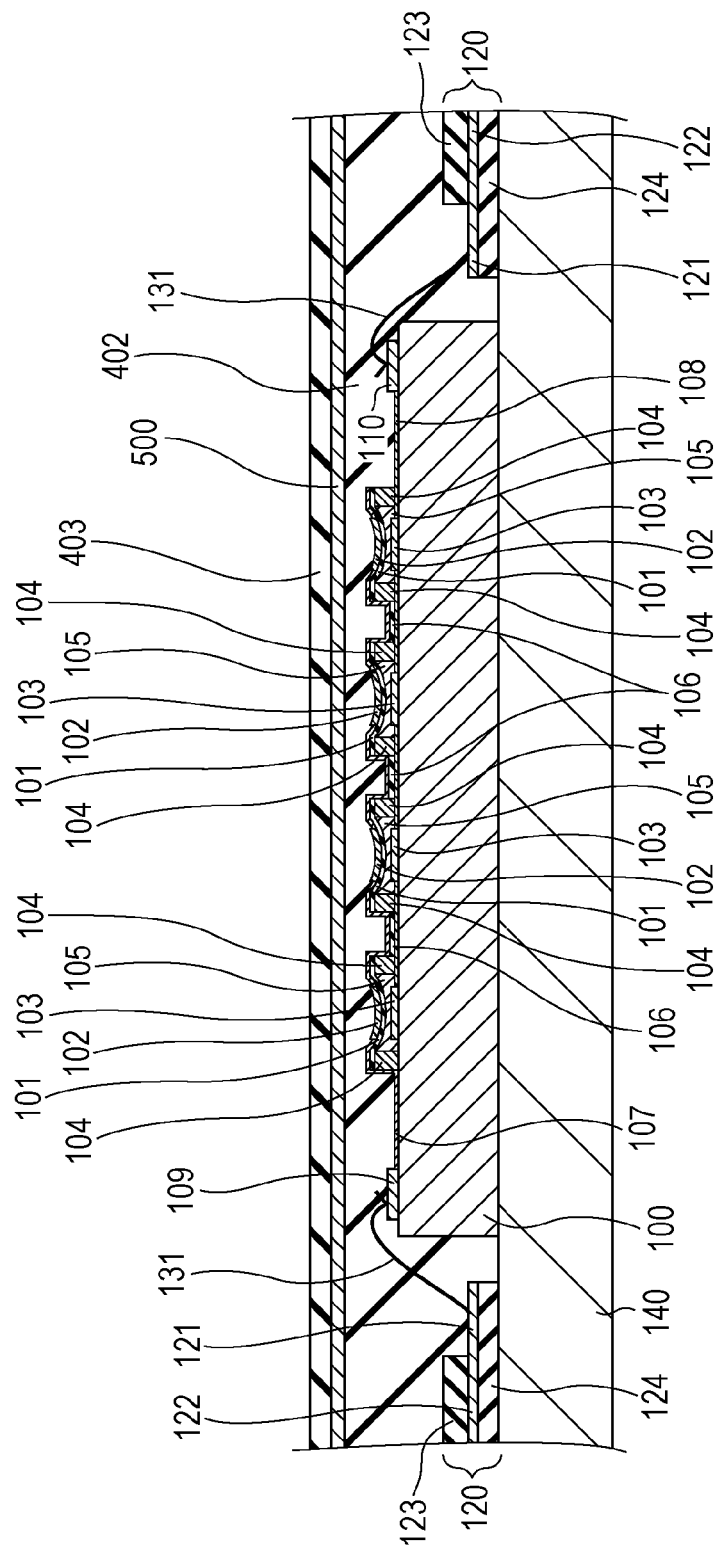

A seventh embodiment differs from the above embodiments in that a layer that supports the electrostatic shield is included. The seventh embodiment is the same as any of the first to sixth embodiments in the other points. FIGS. 10A and 10B are schematic cross-sectional views for describing a capacitive transducer according to the seventh embodiment.

The seventh embodiment is characterized in that an insulating film provided with the electrostatic shield is used. Specifically, the electrostatic shield is arranged on the insulating film. An insulating film 403 may be formed of a thin insulating film and may be made of a material that can be formed into a thin film, such as polyethylene terephthalate (PET), polyimide (PI), polyethylene (PE), or methylpentene (TPX). The insulating film 403 is set so as to have a thickness that is sufficiently small for the wavelength of the ultrasonic waves that are used and desirably has a thickness of several micrometers to a dozen or so micrometers.

FIG. 10A is a schematic view in a configuration in which the seventh embodiment is applied to the configuration of the first embodiment (refer to FIGS. 1A and 1B). FIG. 10B is a schematic view in a configuration in which the seventh embodiment is applied to the configuration of the third embodiment (refer to FIG. 4). The seventh embodiment is not limited to these configurations and may be applied to the configurations of the other embodiments in the same manner.

Since the electrostatic shield layer is formed on the flat insulating film 403 for usage in the seventh embodiment, the uniform and excellent film is provided even when the thickness of the electrostatic shield layer is decreased. Accordingly, the resistance of the electrostatic shield is sufficiently suppressed. Since the thickness of the electrostatic shield layer is decreased, the transmission characteristics of the ultrasonic waves through the electrostatic shield are greatly reduced.

When the seventh embodiment is used in the fifth embodiment or the sixth embodiment, the formation of the electrostatic shield layer on the insulating film provides the electrostatic shield having a shape more close to the desired shape because the electrostatic shield layer has a pattern. When the seventh embodiment is used in the fourth embodiment in which the electrostatic shield is limitedly arranged in a certain area, the manufacturing method is further simplified because the insulating film 403 is easily aligned with the chip 100. When the seventh embodiment is used in the sixth embodiment, the openings of the electrostatic shield are easily aligned with the cells on the chip 100 with high accuracy because the insulating film 403 is easily and accurately aligned with the chip 100. Accordingly, the parasitic capacitance is more effectively reduced. Furthermore, when the seventh embodiment is used in the sixth embodiment, the parasitic capacitance is more effectively reduced because the alignment of the patterns of the multiple electrostatic shield layers is performed with high accuracy.

<Eighth Embodiment>

The capacitive transducer according to any of the first to seventh embodiments is capable of being used for the reception of the photoacoustic waves (the ultrasonic waves) using the photoacoustic effect and is applicable to a sample information acquisition apparatus using the capacitive transducer.

Figure 11:
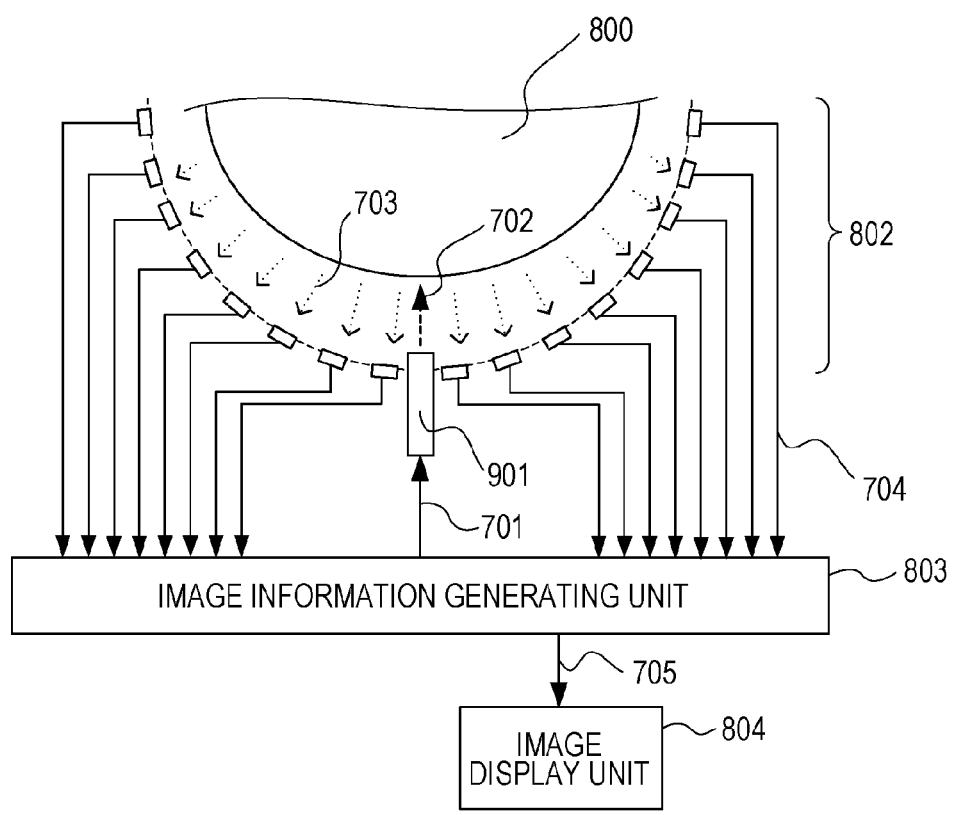
FIG. 11 is a diagram for describing a sample information acquisition apparatus according to an eighth embodiment.

An exemplary operation of a sample information acquisition apparatus of an eighth embodiment will now be specifically described with reference to FIG. 11. First, a light source 901 is caused to generate light 702 (pulsed light) on the basis of a light emitting instruction signal 701 to irradiate the sample (object to be measured) 800 with the light 702. Photoacoustic waves (ultrasonic waves) 703 are generated in the object 800 to be measured in response to the irradiation with the light 702 and the ultrasonic waves 703 are received by multiple capacitive transducers 802 in an ultrasound probe. Information about the size, the shape, and the time of the reception signals are supplied to an image information generating unit 803, which is a processing unit, as reception signals 704 of the photoacoustic waves. Information (light emission information) about the size, the shape, and the time of the light 702 generated in the light source 901 is stored in the image information generating unit 803 for the photoacoustic signals. In the image information generating unit 803 for the photoacoustic signals, an image signal of the object 800 to be measured is generated on the basis of the reception signals 704 of the photoacoustic waves and the light emission information and the generated image signal is supplied to an image display unit 804 as reproduced image information 705 generated from the photoacoustic signals. In the image display unit 804, an image of the object 800 to be measured is displayed on the basis of the reproduced image information 705 generated from the photoacoustic signals. As described above, in the eighth embodiment, the capacitive transducers receive the photoacoustic waves generated by the irradiation of the sample with the light generated by the light source and the processing unit (a sample image information generating unit here) acquires information about the sample using photoacoustic reception signals.

Since the reception characteristics of the capacitive transducers according to the eighth embodiment are less affected by the electric charge of the sample, the capacitive transducers are capable of acquiring the accurate information from the photoacoustic waves. Accordingly, the capacitive transducers are capable of generating a high-quality image.

<Ninth Embodiment>

Figure 12:
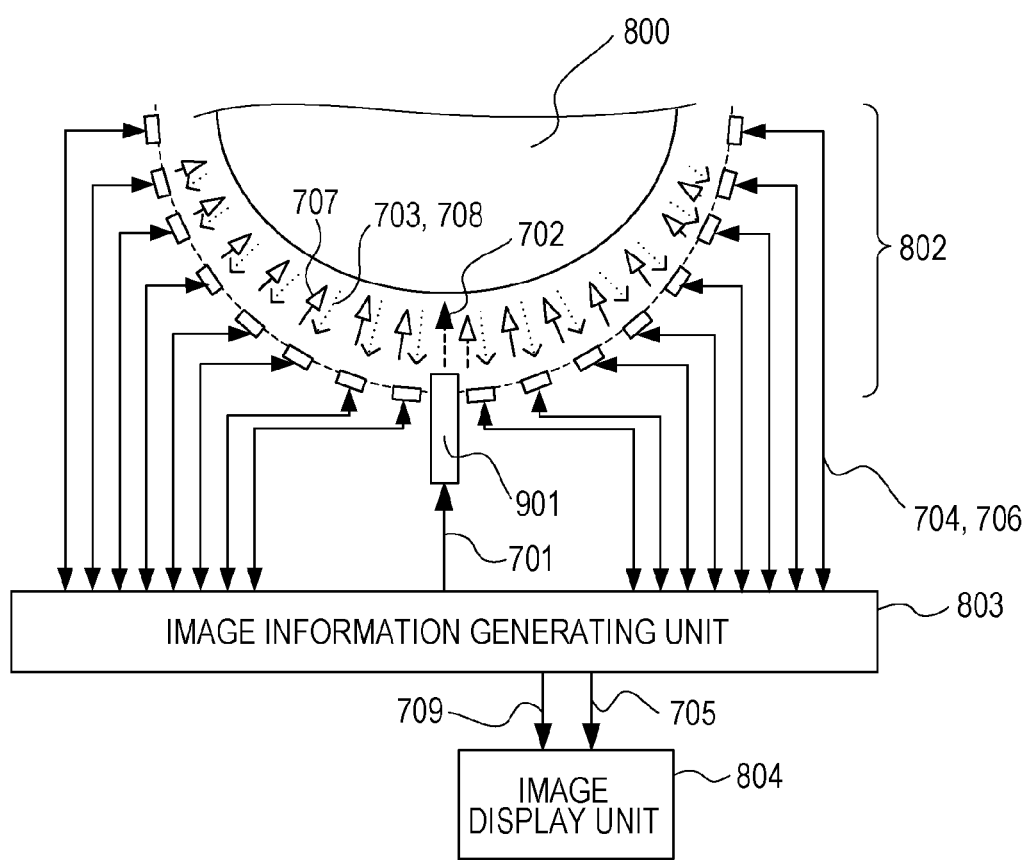
FIG. 12 is a diagram for describing a sample information acquisition apparatus according to a ninth embodiment.
Figure 13:
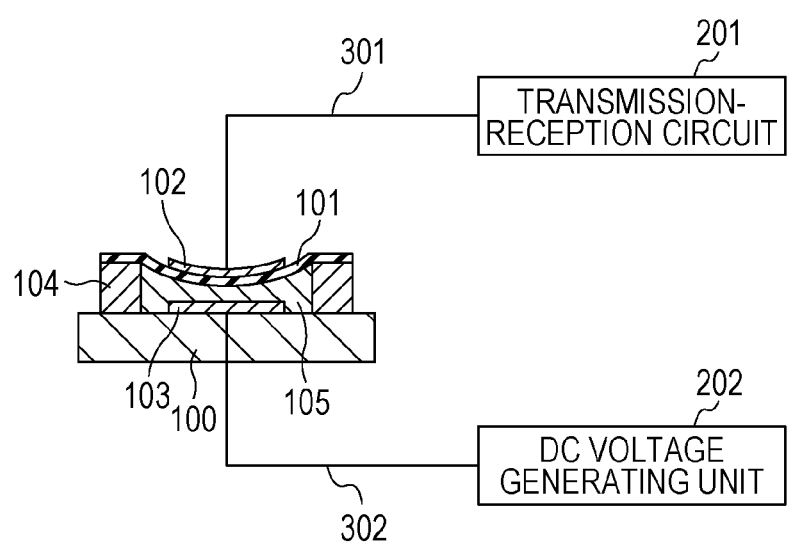
FIG. 13 is a cross-sectional view for describing a capacitive ultrasonic transducer in related art.

In a ninth embodiment, the capacitive transducer according to any of the first to seventh embodiments is used in a sample information acquisition apparatus in a mode different from that of the eighth embodiment. FIG. 12 is a schematic view of a sample information acquisition apparatus according to the ninth embodiment. Referring to FIG. 12, reference numeral 706 denotes ultrasonic transmission-reception signals, reference numeral 707 denotes transmitted ultrasonic waves, reference numeral 708 denotes reflected ultrasonic waves, and reference numeral 709 denotes reproduced image information generated through transmission and reception of the ultrasonic waves. The same reference numerals are used in FIG. 12 to identify the same components illustrated in FIG. 11. The image information generating unit, which is the processing unit, uses a pulse echo method (transmission and reception of the ultrasonic waves), in addition to the reception of the photoacoustic waves, to form an image. Since the reception of the photoacoustic waves is performed in the same manner as that in the eighth embodiment, the pulse echo method (transmission and reception of the ultrasonic waves) will be described here.

The ultrasonic waves 707 are output (transmitted) from the multiple capacitive transducers 802 to the object 800 to be measured on the basis of the ultrasonic transmission signals 706. The ultrasonic waves are reflected in the object 800 to be measured due to the difference in acoustic impedance specific to the substance existing in the object 800 to be measured. The reflected ultrasonic waves 708 are received by the multiple capacitive transducers 802 and information about the size, the shape, and time of the received signals are supplied to the image information generating unit 803 as the ultrasonic reception signals 706. Information about the size, the shape, and the time of the transmitted ultrasonic waves is stored in the image information generating unit 803 as ultrasonic transmission information. An image signal of the object 800 to be measured is generated in the image information generating unit 803 on the basis of the ultrasonic reception signals 706 and the ultrasonic transmission information and the image signal is output as the reproduced image information 709 generated through transmission and reception of the ultrasonic waves.

An image of the object 800 to be measured is displayed in the image display unit 804 on the basis of the reproduced image information 705 generated from the photoacoustic signal and the reproduced image information 709 generated through transmission and reception of the ultrasonic waves. Since the transmission and reception characteristics of the ultrasonic waves in the capacitive transducers in the ninth embodiment are less affected by the electric charge of the sample, reception information from a different measurement method, that is, the transmission and reception of the ultrasonic waves is also capable of being accurately acquired, in addition to the photoacoustic waves, to form an image. Accordingly, it is possible to accurately acquire an image having a greater amount of information and display the image.

In the ninth embodiment, the capacitive transducers at least receive the ultrasonic waves from the sample and the processing unit acquires information about the sample using the ultrasonic reception signals from the capacitive transducers. Although the capacitive transducers also transmit the ultrasonic waves to the sample, the transmission of the ultrasonic waves may be performed by another transducer. Although the capacitive transducers also receive the photoacoustic waves generated in response to the irradiation of the sample with the light generated by the light source and the processing unit acquires information about the sample also using the photoacoustic reception signals, the capacitive transducers may receive only the ultrasonic waves without receiving the photoacoustic waves.

According to the present invention, the provision of the electrostatic shield allows the capacitive transducer having excellent transmission and reception characteristics to be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-236048, filed in Nov. 20, 2014, which is hereby incorporated by reference herein in its entirety.

What is claimed is:

1. A capacitive transducer comprising:
 a substrate;
 at least one cell formed on the substrate and configured to include a first electrode and a vibrating membrane including a second electrode provided so as to be apart from the first electrode with a cavity sandwiched between the first electrode and the second electrode;
 a silicone rubber layer formed on the cell, the silicone rubber layer permits the vibrating membrane to vibrate;
 an electrostatic shield provided on the cell via the silicone rubber layer; and
 a conductive line connected to the first electrode and another conductive line connected to the second electrode,
 wherein the first electrode, the conductive line connected to the first electrode, the second electrode and the another conductive line connected to the second electrode are sandwiched between the electrostatic shield and the substrate.

2. The capacitive transducer according to claim 1, wherein a transmission-reception circuit is connected to the first electrode.

3. The capacitive transducer according to claim 1, wherein a transmission-reception circuit is connected to the second electrode.

4. The capacitive transducer according to claim 1, wherein the first electrode is formed on a chip and includes a plurality of elements each including at least one cell.

5. The capacitive transducer according to claim 4, further comprising:
 a flexible wire configured to be opposed to a face of the chip on which the cell is provided and configured to be electrically connected to an external connection electrode on the face as a wire that connects the first electrode to a direct-current voltage generating unit or a transmission-reception circuit outside the capacitive transducer.

6. The capacitive transducer according to claim 4, further comprising:
 a flexible wire configured to be opposed to a face of the chip on which the cell is provided and configured to be electrically connected to an external connection electrode on the face as a wire that connects the second electrode to a direct-current voltage generating unit or a transmission-reception circuit outside the capacitive transducer.

7. The capacitive transducer according to claim 4, further comprising:
 a flexible wire configured to be opposed to a face opposite to a face of the chip on which the cell is provided and configured to be electrically connected to an external connection electrode on the opposite face as a wire that connects the first electrode to a direct-current voltage generating unit or a transmission-reception circuit outside the capacitive transducer.

8. The capacitive transducer according to claim 4, further comprising:
 a flexible wire configured to be opposed to a face opposite to a face of the chip on which the cell is provided and configured to be electrically connected to an external connection electrode on the opposite face as a wire that connects the second electrode to a direct-current voltage generating unit or a transmission-reception circuit outside the capacitive transducer.

9. The capacitive transducer according to claim 1, further comprising:
 an acoustic lens on the electrostatic shield.

10. The capacitive transducer according to claim 9, wherein the acoustic lens is bonded to the electrostatic shield via the silicone rubber layer.

11. The capacitive transducer according to claim 1, wherein the electrostatic shield is at least arranged at a position opposed to the cell.

12. The capacitive transducer according to claim 1, wherein the electrostatic shield includes an electrostatic shield layer that has no opening and that is uniformly extended.

13. The capacitive transducer according to claim 1, wherein the electrostatic shield includes a plurality of openings viewed from above the cell.

14. The capacitive transducer according to claim 13, wherein the plurality of openings of the electrostatic shield are regularly arranged at positions opposed to the cell.

15. The capacitive transducer according to claim 13, wherein the plurality of openings of the electrostatic shield are arranged at positions corresponding to areas shifted from the cell.

16. The capacitive transducer according to claim 1, wherein the electrostatic shield is composed of a single electrostatic shield layer.

17. The capacitive transducer according to claim 1, wherein the electrostatic shield is composed of a plurality of electrostatic shield layers.

18. The capacitive transducer according to claim 16, wherein the electrostatic shield is composed of a metal layer.

19. The capacitive transducer according to claim 16, wherein the electrostatic shield is arranged on an insulating film.

20. A sample information acquisition apparatus comprising:
 the capacitive transducer according to claim 1; and
 a processing unit,
 wherein the capacitive transducer at least receives ultrasonic waves from a sample, and
 wherein the processing unit acquires information about the sample using an ultrasonic reception signal from the capacitive transducer.

21. The sample information acquisition apparatus according to claim 20,
 wherein the capacitive transducer also transmits ultrasonic waves to the sample.

22. The sample information acquisition apparatus according to claim 20, further comprising:
 a light source,
 wherein the capacitive transducer also receives photoacoustic waves generated in response to irradiation of the sample with light generated by the light source, and
 wherein the processing unit acquires the information about the sample also using a photoacoustic reception signal.

23. A sample information acquisition apparatus comprising:
the capacitive transducer according to claim 1;
a light source; and
a processing unit,
wherein the capacitive transducer receives photoacoustic waves generated in response to irradiation of a sample with light generated by the light source, and
wherein the processing unit acquires information about the sample using a photoacoustic reception signal.

24. The sample information acquisition apparatus according to claim 20, wherein the processing unit is a sample image information generating unit.

25. A capacitive transducer comprising:
a substrate, at least one cell, a silicone rubber layer and an electrostatic shield which are stacked in this order,
wherein the cell includes a first electrode and a vibrating membrane including a second electrode provided so as to be apart from the first electrode with a cavity sandwiched between the first electrode and the second electrode,
wherein a conductive line is connected to the first electrode and another conductive line is connected to the second electrode, and
wherein the first electrode, the conductive line connected to the first electrode, the second electrode, and the another conductive line connected to the second electrode are sandwiched between the electrostatic shield and the substrate.

26. The capacitive transducer according to claim 24, wherein the electrostatic shield includes aluminum, copper, nickel, or gold.

27. The capacitive transducer according to claim 1, wherein the electrostatic shield includes aluminum, copper, nickel, or gold.

* * * * *